US008123741B2

(12) United States Patent
Marrouche et al.

(10) Patent No.: US 8,123,741 B2
(45) Date of Patent: *Feb. 28, 2012

(54) TREATING INTERNAL BODY TISSUE

(75) Inventors: Nassir Marrouche, Cleveland Heights, OH (US); Daniel M. Lafontaine, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 78 days.

This patent is subject to a terminal disclaimer.

(21) Appl. No.: 12/428,719

(22) Filed: Apr. 23, 2009

(65) Prior Publication Data

US 2009/0209951 A1    Aug. 20, 2009

Related U.S. Application Data

(63) Continuation of application No. 11/082,677, filed on Mar. 17, 2005, now Pat. No. 7,674,256.

(51) Int. Cl.
*A61B 18/02* (2006.01)
*A61B 18/04* (2006.01)

(52) U.S. Cl. ............................... 606/21; 606/23; 606/28

(58) Field of Classification Search ............ 606/21, 606/23, 28

See application file for complete search history.

(56) References Cited

U.S. PATENT DOCUMENTS

| | | |
|---|---|---|
| 4,404,971 A | 9/1983 | LeVeen et al. |
| 4,718,421 A | 1/1988 | Rohwedder et al. |
| 4,744,366 A | 5/1988 | Hang |
| 4,906,244 A | 3/1990 | Pinchuk et al. |
| 4,955,377 A | 9/1990 | Lennox et al. |
| 5,304,121 A | 4/1994 | Sahatjian |
| 5,372,587 A | 12/1994 | Hammerslag et al. |
| 5,423,807 A | 6/1995 | Milder |
| 5,439,443 A | 8/1995 | Miyata et al. |
| 5,447,497 A | 9/1995 | Sogard et al. |
| 5,509,417 A | 4/1996 | Dias et al. |
| 5,536,252 A | 7/1996 | Imran et al. |
| 5,540,679 A | 7/1996 | Fram et al. |
| 5,545,133 A | 8/1996 | Burns et al. |
| 5,575,766 A | 11/1996 | Swartz et al. |
| 5,575,772 A | 11/1996 | Lennox |

(Continued)

FOREIGN PATENT DOCUMENTS

EP    1 042 990    10/2000

(Continued)

OTHER PUBLICATIONS

Hendry et al., "Argon Beam Coagulation Compared with Cryoablation of Ventricular Subendocardium," *Ann. Thorac. Surg.*, 1993, 55(1):135-139.

(Continued)

*Primary Examiner* — Lee Cohen
(74) *Attorney, Agent, or Firm* — Fish & Richardson P.C.

(57) ABSTRACT

Some embodiments of the invention relate to a system for treating tissue internal to a body, such as heart tissue. For example, the system may be used to ablate tissue as a treatment for atrial fibrillation. In certain embodiments, the system is capable of causing scar tissue to form in ostial areas of the atrium rather than inside the pulmonary vein. In such embodiments, the system may include a tissue treatment member that is operable to form an annular area of ablated tissue along the outer portion of the ostium in an area known as the antrum.

74 Claims, 9 Drawing Sheets

U.S. PATENT DOCUMENTS

| | | | |
|---|---|---|---|
| 5,582,609 | A | 12/1996 | Swanson et al. |
| 5,590,657 | A | 1/1997 | Cain et al. |
| 5,630,837 | A | 5/1997 | Crowley |
| 5,680,860 | A | 10/1997 | Imran |
| 5,704,361 | A | 1/1998 | Seward et al. |
| 5,797,842 | A | 8/1998 | Pumares et al. |
| 5,868,735 | A | 2/1999 | Lafontaine |
| 5,938,660 | A | 8/1999 | Swartz et al. |
| 5,971,979 | A | 10/1999 | Joye et al. |
| 5,971,983 | A | 10/1999 | Lesh |
| 6,012,457 | A | 1/2000 | Lesh |
| 6,024,703 | A | 2/2000 | Zanelli et al. |
| 6,149,599 | A | 11/2000 | Schlesinger et al. |
| 6,156,053 | A | 12/2000 | Gandhi et al. |
| 6,290,696 | B1 | 9/2001 | Lafontaine |
| 6,305,378 | B1 | 10/2001 | Lesh |
| 6,416,511 | B1 | 7/2002 | Lesh et al. |
| 6,416,533 | B1 | 7/2002 | Gobin et al. |
| 6,432,102 | B2 | 8/2002 | Joye et al. |
| 6,451,044 | B1 | 9/2002 | Naghavi et al. |
| 6,474,340 | B1 | 11/2002 | Vaska et al. |
| 6,475,210 | B1 | 11/2002 | Phelps et al. |
| 6,500,174 | B1 | 12/2002 | Maguire et al. |
| 6,514,245 | B1 | 2/2003 | Williams et al. |
| 6,595,988 | B2 | 7/2003 | Wittenberger et al. |
| 6,595,989 | B1 | 7/2003 | Schaer |
| 6,602,276 | B2 | 8/2003 | Dobak, III et al. |
| 6,605,084 | B2 | 8/2003 | Acker et al. |
| 6,605,106 | B2 | 8/2003 | Schwartz |
| 6,610,058 | B2 | 8/2003 | Flores |
| 6,620,131 | B2 | 9/2003 | Pham et al. |
| 6,635,054 | B2 | 10/2003 | Fjield et al. |
| 6,648,878 | B2 | 11/2003 | Lafontaine |
| 6,652,517 | B1 | 11/2003 | Hall et al. |
| 6,709,431 | B2 | 3/2004 | Lafontaine |
| 6,758,830 | B1 | 7/2004 | Schaer et al. |
| 7,008,418 | B2 * | 3/2006 | Hall et al. .................. 606/41 |
| 7,022,120 | B2 | 4/2006 | Lafontaine |
| 7,674,256 | B2 * | 3/2010 | Marrouche et al. ............ 606/21 |
| 2002/0091378 | A1 | 7/2002 | Dobak et al. |
| 2003/0050637 | A1 | 3/2003 | Maguire et al. |
| 2004/0049176 | A1 | 3/2004 | Lafontaine |
| 2004/0092870 | A1 | 5/2004 | Squire et al. |
| 2004/0243124 | A1 | 12/2004 | Im et al. |
| 2005/0038419 | A9 | 2/2005 | Arnold et al. |
| 2005/0124843 | A1 | 6/2005 | Singh |
| 2005/0273095 | A1 | 12/2005 | Taimisto et al. |
| 2006/0178663 | A1 | 8/2006 | LaFontaine |
| 2007/0021746 | A1 | 1/2007 | Taimisto et al. |
| 2007/0270789 | A1 | 11/2007 | Berger |

FOREIGN PATENT DOCUMENTS

| | | |
|---|---|---|
| EP | 1 424 100 | 6/2004 |
| GB | 1019028 | 2/1966 |
| GB | 2 321 853 | 12/1998 |
| GB | 2336782 | 11/1999 |
| GB | 2337000 | 11/1999 |
| WO | WO 95/01751 | 1/1995 |
| WO | WO 97/12557 | 4/1997 |
| WO | WO 98/52465 | 11/1998 |
| WO | WO 99/02096 | 1/1999 |
| WO | WO 99/27862 | 6/1999 |
| WO | WO 99/33391 | 7/1999 |
| WO | WO 00/45706 | 8/2000 |
| WO | WO 00/47118 | 8/2000 |
| WO | WO 01/37925 | 5/2001 |

OTHER PUBLICATIONS

Ross et al., "Cardiac Rhythm Disturbances due to Caval Occlusion During Hepatic Cryosurgery," *Cryobiology*, 1994, 31(5):501-505.

Gregori et al., "Cox Maze Operation Without Cryoablation for the Treatment of Chronic Atrial Fibrillation," *Ann. Thorac. Surg.*, 1995, 60(2):361-363.

Fujino et al., "Histologic Study of Chronic Catheter Cryoablation of Atrioventricular Conduction in Swine," *Am. Heart J.*, 1993, 125(6):1632-1637.

Gaer et al., "Intractable Chest Pain in Cardiomyopathy: Treatment by a Novel Technique of Cardiac Cryodenervation with Quantitative Immunohistochemical Assessment of Success,", *Br. Heart J.*, 1993, 70(6):574-577.

Gaymes et al., "Percutaneous Serial Catheterization in Swine: a Practical Approach," *J. Invest. Surg.*, 1995, 8(2):123-128.

Stephenson et al., "Renal Cryoablation in a Canine Model," *Urology*, 1996, 47(5):772-776.

"Prostate cryosurgery now reimbursable in Southern California," *Healthcare Technology Management*, Oct. 1999, p. 22.

Cahan, "Five Years of Cryosurgical Experience: Benign and Malignant Tumors with Hemorrhagic Condition," *Cryosurgery*, published on date even with or prior to Jan. 12, 1999, pp. 388-391.

Coger et al., "Preservation Techniques for Biomaterials," *The Biomedical Engineering Handbook*, 1995, pp. 1567-1577.

Fuller et al., "Clinical Applications of Cryobiology," published on date even with or prior to Jan. 12, 1999, 4 pages.

Hunt et al., "Fractures in Cryopreserved Arteries," *Cryobiology*, 1994, 31:506-515.

Mazur, "Physical-Chemical Factors Underlying Cell Injury in Cryosurgical Freezing," *Cryosurgery*, published on date even with or prior to Jan. 12, 1999, pp. 32-51.

Morris et al., "Effects of Low Temperatures on Biological Membranes," published on date even with or prior to Jan. 12, 1999, 2 pages.

Nataf et al., "Effect of Cold Anoxia and Cryopreservation on Metabolic and Contractile Functions of Human Mammary Artery," *Cryobiology*, 1995, 32:327-333.

Schilling et al., "Nature of the Vehicle for Cryopreservation of Human Peripheral Veins: Preservation of Reactivity to Pharmacological Stimuli," *Cryobiology*, 1995, 32:109-113.

Stephenson et al., "Renal Cryoablation in a Canine Model," *Urology*, 1996, 47(5)72-776.

Zacarian, "Cryosurgery of Tumors of the Skin and Oral Cavity," published on date even with or prior to Jan. 12, 1999, 5 pages.

* cited by examiner

TREATING INTERNAL BODY TISSUE

CROSS-REFERENCE TO RELATED APPLICATION(S)

This application is a continuation of U.S. patent application Ser. No. 11/082,677 filed on Mar. 17, 2005 by Marrouche et al., now U.S. Pat. No. 7,674,256, the contents of which are fully incorporated herein by reference.

TECHNICAL FIELD

This document relates to treating internal body tissue, such as ablating heart tissue.

BACKGROUND

A normal heart beat initiates at the sinoatrial node, located proximal the right atrium of the heart. The sinoatrial node causes electrical impulses to spread through the right and left atria, which in turn causes the atria to contract. The impulses travel to the atrioventricular node and then through the walls of the ventricles, thereby causing the ventricles to contract. Such contractions force blood out of the heart to the lungs and body. When the heart operates under a regular pattern of electrical impulses, the heart beats at a generally constant rhythm—filling with blood and contracting in a normal fashion.

Atrial fibrillation is a common source of irregular heart rhythms. It affects millions of people in the United States, and thousand of new cases of atrial fibrillation are diagnosed each year. When a patient suffers from atrial fibrillation, irregular electrical impulses begin and spread through the atria. The resulting rhythm is disorganized and inconsistent. The atria do not contract in a regular rhythm because the impulses are traveling through the atria in a disorderly fashion.

Patients who suffer from atrial fibrillation may experience various symptoms, such as heart palpitations, a lack of energy, dizziness, chest pains, pressure or discomfort in the chest, and breathing difficulty. Some people may have atrial fibrillation without exhibiting any symptoms at all, but chronic atrial fibrillation can result in future problems including blood clotting (increased risk of suffering a stroke) and heart failure.

Various options may be used to treat atrial fibrillation and to restore normal heart rhythm. For example, a patient with atrial fibrillation may receive medications or a pacemaker device to prevent blood clots and control the heart rate. In some circumstances, heart surgery may be performed to treat atrial fibrillation. For example, the Cox-Maze procedure is a surgery that may require an incision in the patient's sternum, and in many instances, requires a heart-lung machine to oxygenate and circulate the blood during surgery.

Another treatment option is catheter ablation therapy. For example, a catheter may be used to perform pulmonary vein isolation ablation, in which a circular balloon at the tip of the catheter is inserted into the pulmonary vein. Material in the balloon at the tip of the catheter is then heated to ablate tissue inside the pulmonary vein. A circular scar is formed in the pulmonary vein as an attempt to create a conduction block to stop passage of irregular impulses firing from within the pulmonary vein. Forming the scar tissue inside the pulmonary vein is not always successful at preventing atrial fibrillation.

The design of the catheter ablation device has an effect on the success rate of the catheter ablation procedures. One factor that affects the design of the catheter ablation device is the efficacy of delivering the ablating energy. If, for example, the catheter device is improperly sized or unable to adjust to the contours of the target tissue, some portion of the target tissue may remain after the ablating procedure. The living tissue may not block the irregular impulses from the pulmonary vein to the atrium, thus permitting future occurrences of atrial fibrillation.

Another factor that affects the design of the catheter ablation device is the isolation of the ablating energy. If, for example, the catheter ablation device does not properly isolate the ablating energy to the target tissue or delivers excess energy, some live tissue in a non-targeted area may be unnecessarily destroyed. In such circumstances, the catheter ablation procedure may cause pulmonary vein stenosis (a narrowing of the passageway), which may result in more serious cardiovascular problems for the patient.

SUMMARY

Some embodiments of the invention relate to a device for treating atrial fibrillation. In certain embodiments, the device is capable of causing scar tissue to form in ostial areas of the atrium rather than inside the pulmonary vein. In such embodiments, the device may include a tissue treatment member that is operable to form an annular area of ablated tissue along the outer portion of the ostium in an area known as the antrum.

A number of embodiments include a system to treat tissue internal to a body. The system includes an elongate member having a proximal portion, a distal portion, and at least one lumen extending therethrough. The system further includes a tissue treatment member disposed at the distal portion of the elongate member. The tissue treatment member is in fluid communication with the lumen. Also, the system includes an anchor member adjustably engaged with the tissue treatment member. When the anchor member is disposed distally of the tissue treatment member and disposed in a position at least partially in a pulmonary vein, the tissue treatment member is annularly adjustable relative to the position of the anchor member so as to contact an ostial area.

Certain embodiments include a system for treating tissue internal to a body. The system includes a catheter assembly having a distal end and a proximal end, and an anchor member disposed near the distal end of the catheter assembly. The anchor member is configured to be received in a pulmonary vein. The system also includes a thermal treatment device engaged with the catheter assembly proximally of the anchor member. The system further includes a steering mechanism disposed at least in part between the anchor member and the thermal treatment device to cause the thermal treatment device to contact one or more ostial areas.

Some embodiments include a method of treating tissue internal to a body. The method includes directing an anchor member at least partially into a pulmonary vein and securing at least a portion of the anchor member to the pulmonary vein. The method further includes directing a tissue treatment member toward an ostium proximate an atrium and the pulmonary vein. Also, the method includes annularly adjusting the tissue treatment member relative to the position of the anchor member so as to treat tissue at an ostial area proximate the atrium and the pulmonary vein.

These and other embodiments may be configured to provide one or more of the following advantages. First, atrial fibrillation may be treated by forming an annular conduction block area along the outer portion of the ostium in an area known as the antrum. By causing scar tissue to form in ostial areas of the atrium rather than in the pulmonary vein, the likelihood of preventing atrial fibrillation may be increased. Second, the tissue treatment member may be used independent of the ostium size near the target site. Even if the tissue treatment member is substantially smaller than the targeted ostial area, it may be adjusted relative to the anchor member to contact the targeted ostial areas. Third, in embodiments where the anchor member can be secured at various locations inside the pulmonary vein, the tissue treatment member can be directed to the ideal ostial area locations. Fourth, in some embodiments where the tissue treatment member uses cryo ablation technology, an annular lesion may be formed in the antrum with as few as one to five cryo lesions, thereby reducing the time required to perform the medical operation. Some or all of these and other advantages may be provided by the embodiments described herein.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
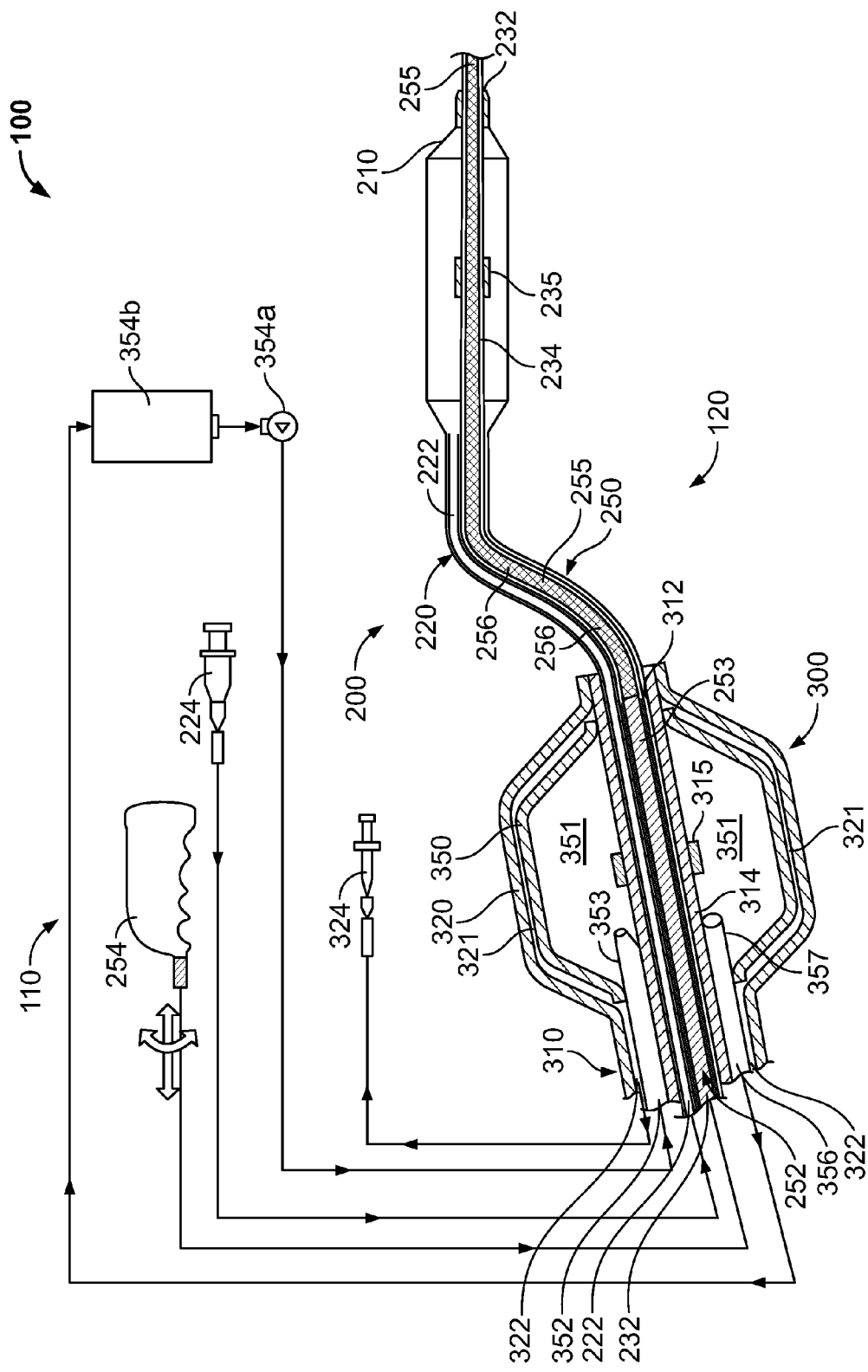
FIG. 1 is a cross-sectional view of a portion of a system for treatment of tissue internal to a body.

Referring to FIG. 1, a system 100 to treat tissue internal to a body includes an anchor member 210 disposed distally of a tissue treatment member 300. A steerable portion 250 is disposed between the anchor member 210 and the tissue treatment member 300 so that the tissue treatment member 300 is adjustable relative to the anchor member 210. The system 100 may include a number of tools at a proximal portion 110 that remain external of a patient's body when in use. Each of the tools at the proximal portion 110 may be used by a medical practitioner to perform various functions at a distal portion 120 of the system 100. Each of the tools may be coupled to one or more associated lumens in the system 100 using one or more manifolds (not shown in FIG. 1) at the proximal portion 110. For the purpose of the following discussion, the depicted embodiments are directed to a system 100 that is particularly suitable for pulmonary vein isolation ablation or other similar treatments. However, with some modifications in construction, the system 100 may be used for other medical applications not fully discussed herein In some embodiments, an anchor device 200 includes an anchor member 210 that is disposed at a distal end of an anchor catheter 220. The anchor member 210 may include an expandable structure, such as a balloon, that is capable of expanding to press against a vein wall. For example, a saline solution may be forced into the anchor member to cause expansion of the balloon structure. Other inflation fluids may also be used, including liquids and gases.

The anchor catheter 220 may include a wall to define an inflation lumen 222 that extends from the proximal portion 110 to the distal portion of the system 100. The inflation lumen 222 is in fluid communication with balloon 210 such that a pressure source, like a plunger disposed in a chamber or a pump device, may deliver pressurized fluid (e.g., saline solution) to expand the balloon 210. In certain embodiments, the pressure source 224 may be in fluid communication with the inflation lumen 222 via a manifold (not shown in FIG. 1) disposed at the proximal portion 110 of the system 100.

Still referring to FIG. 1, in embodiments in which the anchor member 210 includes a balloon, the anchor balloon 210 may include one of a number of constructions. The material of the anchor balloon 210 may be selected from polymers including, but not limited to, polyolefin copolymer, polyester, polyethylene teraphthalate, polyethylene, polyether-block-amide, polyamide, polyimide, nylon, latex and urethane. The anchor balloon 210 may be made by blow molding a polymer extrusion into the desired shape. In some embodiments, the anchor balloon 210 may be constructed to expand to the desired shape when pressurized, but the balloon 210 will not elastically deform substantially beyond the desired shape. A number of ancillary processes may be used to affect the material properties of the anchor balloon 210. For example, the polymer extrusion may be exposed to gamma radiation which alters the polymer infrastructure to provide uniform expansion during blow molding and additional burst strength when in use. In addition, the molded balloon 210 may be exposed to a low temperature plasma field which alters the surface properties of the balloon 210 to provide enhanced adhesion characteristics. Those skilled in the art will recognize that other materials and manufacturing processes may be used to provide a balloon 210 suitable for use with the system 100.

In some embodiments, the anchor catheter 220 may include a guide wire lumen 232 that extends from the proximal portion 110 to the distal portion 120. The guide wire lumen 232 may be adjacent to the inflation lumen 222, as shown in FIG. 1. In this embodiment, the guide wire lumen 232 includes a tubular wall 234 that extends through the catheter 220 and the balloon 210 such that the anchor device 200 may slidably pass over a wire structure that is disposed in the guide wire lumen 232. As such, the anchor member 210 (e.g., anchor balloon) may be guided to a target site internal to a body by sliding the anchor device 200 over a guide wire 252 that was previously directed to the target site. A marker band 235 may be attached to the tubular wall 234 in the balloon 210 so that the position of the balloon 210 in the patient's body may be visualized using known imaging techniques.

In this embodiment, an over-the-wire manifold (not shown in FIG. 1) may be coupled to the guide wire lumen 232 at the proximal portion 110 of the system 100 so that a guide wire instrument 252 can be controlled and adjusted at the proximal portion 110. For example, the guide wire instrument 252 may be coupled with a handle member 254 that may be grasped by a physician near the proximal portion 110 so that the guide wire instrument 252 may be slidably adjusted relative to the anchor device 200 at the distal portion 120. Such a handle member 254 allows the treating physician to more easily grip and manipulate the guide wire instrument 252. Optionally, the manifold may also incorporate a strain relief device (not shown in FIG. 1) to reduce the likelihood of kinking the guide wire instrument 252.

While the embodiment depicted in FIG. 1 shows a construction in which the guide wire lumen 232 is adjacent to the inflation lumen 232, it is also contemplated that a coaxial construction or other appropriate arrangement may be used. In the coaxial construction, the guide wire lumen 232 would extend inside the inflation lumen 222. The inflation lumen 222 would have a larger relative diameter than the non-coaxial embodiment so as to accommodate the tubular wall around the guide wire lumen 232. A support connection may be desired between the tubular wall around guide wire lumen 232 and the wall around the inflation lumen 222 that would prevent relative longitudinal movement therebetween while allowing an inflation fluid to pass through.

Still referring to FIG. 1, the tissue treatment member 300 is disposed near a distal end of an elongate member 310 that extends from the proximal portion 110 of the system 100 to the distal portion 120. In some embodiments, the tissue treatment member 300 includes a cryo ablation device that is capable of contacting an ostial area near a pulmonary vein. In such embodiments, the tissue treatment member 300 may have an one or more balloons adapted to deliver cryo treatment to nearby tissue—similar to certain features of particular embodiments described in U.S. Pat. No. 5,868,735 to Lafontaine, which is incorporated herein by reference. The tissue treatment member 300 may also include a guide lumen 312 through which the anchor device 200 (and the guide wire instrument 252 therein) may pass. While the embodiment depicted in FIG. 1 shows a construction for use in cryo ablation therapy, it is contemplated that other embodiments may include a tissue treatment member having a construction for use with RF energy ablation. For example, a tissue treatment member 300 may include a single balloon having electrodes disposed therein and being expandable with application of a chemical solution that can be heated using RF energy.

In the embodiment shown in FIG. 1, the elongate member 310 has one or more lumens extending therethrough, each of which may be coupled to an associated manifold (not shown in FIG. 1) at the proximal portion 110. For example, the elongate member 310 may include a catheter that has a plurality of coaxial lumens—a vacuum lumen 322 in fluid communication with an external balloon 320 and has a guide lumen 312 that permits the tissue treatment member 300 to be slidably engaged with the anchor catheter 220. The vacuum lumen 322 is in fluid communication with the external balloon 320 such that a vacuum source 324, such as a plunger disposed in a chamber or a vacuum pump device, may withdraw fluid from a safety chamber 321 in the external balloon 320. The vacuum source 324 may be in fluid communication with the vacuum lumen 322 via a manifold (not shown in FIG. 1) disposed at the proximal portion 110 of the system 100. The safety chamber 321 may be defined by the external balloon 320 and may be sized to fit over the internal balloon 350 when coolant is cycled through the coolant chamber 351 (described in more detail below). For example, the safety chamber 321 may be evacuated by application of a vacuum from the vacuum source 324. When the coolant material is cycled through the coolant chamber 351 to inflate the internal balloon 350, the external balloon 320 may inflate with the internal balloon 350. (The gap between the external balloon 320 and the internal balloon 350 is shown in FIG. 1 for illustrative purposes only. It should be understood that at least a portion of the external balloon 320 may contact the internal balloon 320 when the safety chamber 321 is evacuated by application of a vacuum.) The external balloon 320 provides a safety feature to reduce the likelihood of coolant seeping into the patient's body in the event that the internal balloon 350 breaks or otherwise permits coolant to leak from the coolant chamber 351. If coolant leaks from the coolant chamber 351, the leaked coolant material would be evacuated from the safety chamber 321 by application of the vacuum force.

The guide lumen 312 may be configured to slidably engage the outer surface of the anchor catheter 220. The guide lumen 312 includes a tubular wall 314 that passes through the tissue treatment member 300 such that a portion of the anchor catheter 220 and the anchor member 210 (e.g., anchor balloon) may be disposed distally from an open end of the guide lumen 312. A marker band 315 may be attached to the tubular wall 314 in the tissue treatment member 300 so that the position of the tissue treatment member 300 in the patient's body may be visualized using known imaging techniques. While the embodiment depicted in FIG. 1 shows a construction in which the vacuum lumen 322 is coaxial with the guide lumen 312, it should be understood other embodiments may include an vacuum lumen 322 that is adjacent to the guide lumen 312.

Still referring to FIG. 1, the elongated member 310 may include an input lumen 352 and an output lumen 356 that are in fluid communication with an internal balloon 350. The input lumen 352 may be defined by an intake tube 353 that extends from the internal balloon 350 to the proximal portion 110 of the system 100. Similarly, the output lumen 356 may be defined by an exhaust tube 357 that extends from the internal balloon 350 to the proximal portion 110 of the system 100. In some embodiments, the distal orifice of the intake tube 353 may have a smaller diameter than the distal orifice of the exhaust tube 357, which can facilitate proper control of the coolant material during cryo ablation procedures. The input lumen 252 is in fluid communication with a valve 354a near the proximate portion 110 of the system 100. The valve 354a is coupled to a coolant source 354b, which may include a refrigeration unit for controlling the temperature of the coolant. A proximal end of the output lumen 356 can be in fluid communication with the coolant source 354b for purposes of recycling the coolant material. Alternatively, the proximal end of the output lumen 356 can be in fluid communication with a drain for disposal of the cycled coolant. In some alternative embodiments, the input and output lumens 352 and 356 may have a coaxial construction. In such embodiments, the input and output lumens may be coaxially disposed around the guide lumen 312.

In some embodiments using cryo ablation technology, the internal balloon 350 defines a coolant chamber 351 where a coolant material may be cycled. The chamber 351 may be sized such that coolant material input from the intake tube 353 evaporates in whole or in part in the chamber 351 before exiting through the exhaust tube 357. The internal balloon 350 may expand to a desired shape when pressurized, but will not elastically deform substantially beyond the desired shape. The material of the internal balloon 350 and the external balloon 320 may vary depending on the coolant type and the conditions within the cooling chamber. In some embodiments, the internal and external balloons 350 and 320 may comprise a polymer material, such as polyolefin copolymer, polyester, polyethylene teraphthalate, polyethylene, polyether-block-amide, polyamide, polyimide, nylon, latex, or urethane. For example, certain embodiments of the tissue treatment member 300 may include an internal balloon 350 comprising PEBAX® 7033 material (70D poly ether amide block). In such examples, the external balloon 320 may also comprise the PEBAX® 7033 material or another appropriate material.

The coolant material that is cycled into the coolant chamber 351 is one that will provide the appropriate heat transfer characteristics consistent with the goals of treatment. In some embodiments, liquid $N_2O$ can be used as a cryogenic fluid. When liquid $N_2O$ is used in the tissue treatment member 300, it can be transported to the coolant chamber 351 in the liquid phase where it evaporates at the orifice of intake tube 353 and exits through the exhaust tube 357 in the gaseous state. Other embodiments of the tissue treatment member 300 may use Freon, Argon gas, and $CO_2$ gas as coolants. Further yet, some embodiments of the tissue treatment member 300 may use coolants (which would enter and exit the coolant chamber 351 as a liquid), such as Fluisol, or a mixture of saline solution and ethanol.

Optionally, the temperature of the tissue treatment member 300 can be monitored by thermo-resistive sensors (not shown in FIG. 1) proximate to the external balloon 320, the internal balloon 350, or both. As described in the previously referenced U.S. Pat. No. 5,868,735 to Lafontaine, the temperature can be monitored either absolutely with pre-calibrated sensors and/or relatively between two or more sensors. Depending on the treatment goals and monitored temperature, the flow rate of the coolant into the catheter can be adjusted to raise or lower the temperature of the tissue treatment member 300.

Still referring to FIG. 1, the system 100 includes a steerable portion 250 disposed between the tissue treatment member 300 and anchor member 210. The steerable portion 250 permits the tissue treatment member 300 to be adjusted relative to the distally positioned anchor member 210. The steerable portion 250 may include various mechanisms to adjust the position of the tissue treatment member 300 relative to the anchor member 210. For example, the steerable portion 250 may include a shape memory element 255 that is movably or fixedly engaged with the anchor device 200, the tissue treatment member 300, or both. The shape memory element 255 may be pre-formed to have a curved portion 256 such that when the shape memory element 255 is rotated, the tissue treatment member 300 is adjusted annularly relative to the anchor member 210. The pre-formed shape memory element may comprise a superelastic Nitnol material that was exposed to austenitic/martensite processing. In an alternative example, the steerable portion 250 may include one or more pull wires that are operated at the proximal portion 110 of the system 100 to control the position of the tissue treatment member 300 relative to the anchor member 210.

In addition, multiple elongate shape memory members may be attached to the walls of the steerable portion 250 at locations in which it is desired to shorten the walls. For example, such element may be placed at the same longitudinal location, and spaced around the periphery guide wire instrument 252 or the anchor catheter 220. In some embodiments, three shape memory wires may be spaced around the periphery of the guide wire instrument 252 at 120-degree separations, which would permit any one or two of those three wires to be shortened (e.g., by applying an electrical charge to the shape memory material) so as to adjust the tissue treatment member 300 relative to the anchor member 210. In another example, the shape memory elements may be positioned at multiple longitudinal locations along the guide wire instrument 252 so as to bend the instrument in multiple directions. In such embodiments, the shape memory elements may be wires that shorten when subjected to an electric current, and which elongated when the current is removed so that controlled application of electrical current may provide steering control.

Figure 2A:
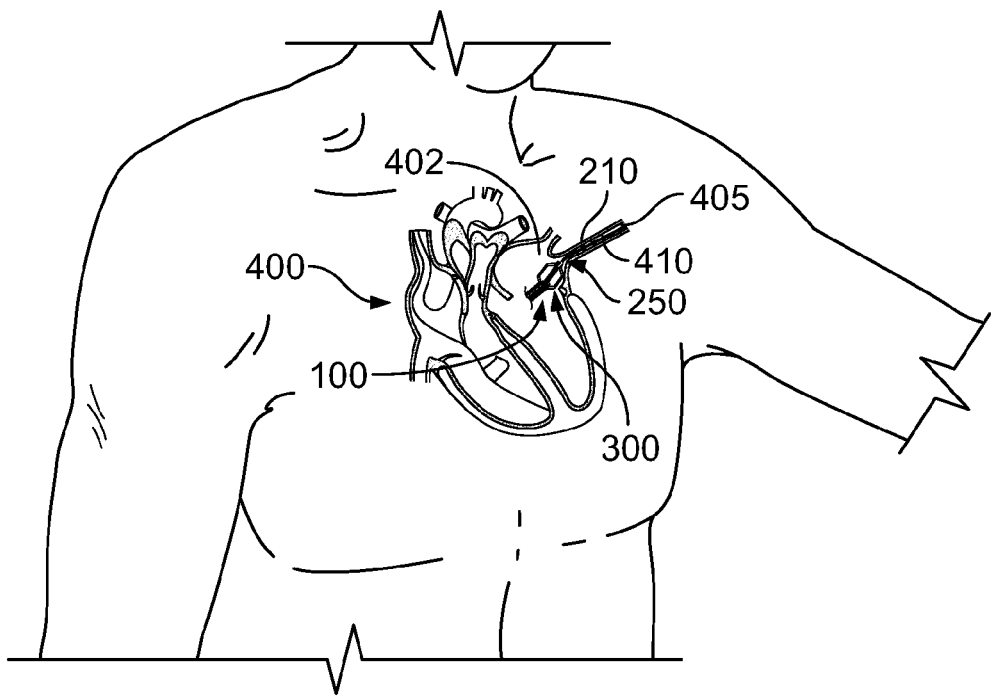
FIGS. 2A-B are views of a cross-section of a heart with a portion of the system of FIG. 1 disposed in the heart.
Figure 2B:
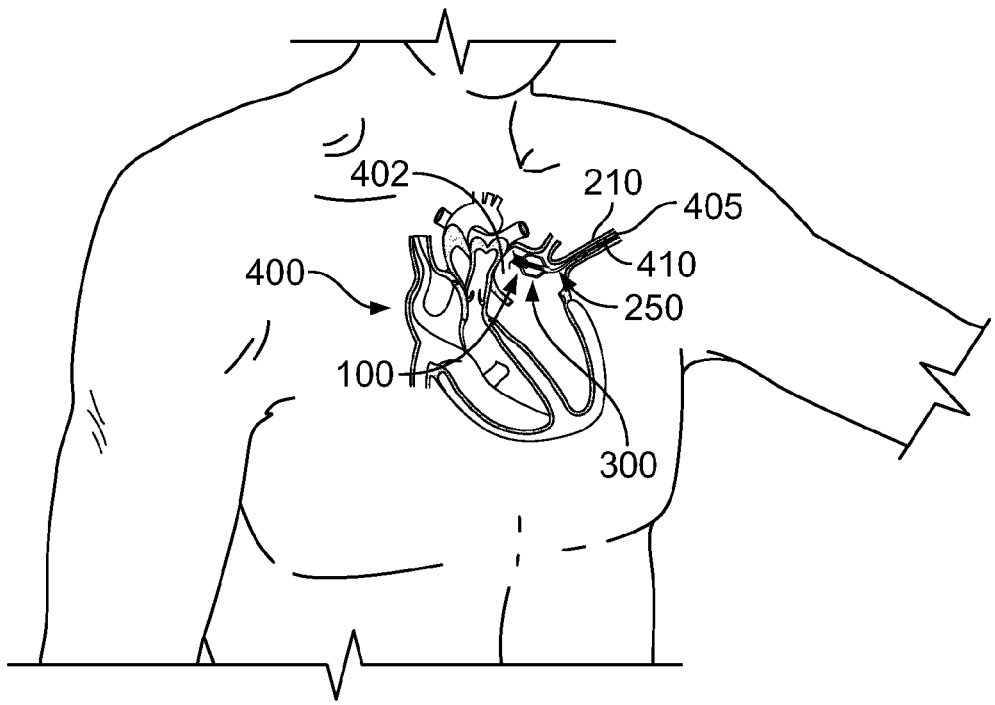

Referring now to FIGS. 2A-B, some embodiments of the system 100 may be configured to ablate tissue in a heart 400. In such embodiments, the tissue treatment member 300 may be directed to ostial areas proximate the left atrium 402 outside a pulmonary vein 405. In the depicted embodiment, the anchor member 210 may include an expandable balloon. As described in more detail below in connection with FIG. 3, the anchor balloon 210 of the anchor device 200 may be sized to press against a wall 410 of a pulmonary vein 405. The anchor balloon 210 is sized to fit in a pulmonary vein 405 and to expand to a desired shape to press against a wall 410 of the pulmonary vein 405. As such, the tissue treatment member 300 may be disposed outside of the pulmonary vein 405 and may be biased against an ostial area in the left atrium 402. For example, the tissue treatment member 300 may be in contact with an outer ostial area in the left atrium 402 known as the antrum. When the coolant is cycled into the chamber 351 (FIG. 1), heat transfer may occur between the contacted ostial area and the tissue treatment member 300. Such heat transfer may cause ablation of tissue cells proximate the ostial area, as described in more detail below.

As shown in FIGS. 2A-B, when a particular ostial area has been ablated by the tissue treatment member 300, the steerable portion 250 may provide the proper guidance to adjust the tissue treatment member 300 to another ostial area so as to form an annular area of ablated tissue along the ostium. The tissue treatment member 300 may be adjusted relative to the anchor balloon 210 as described below in connection with FIG. 3. Because the tissue treatment member 300 can be adjusted relative to the anchor member 210 in the pulmonary vein 405, the system 100 may perform catheter ablation therapy independent of the ostium size in the left atrium 402. For example, if an outer diameter of the tissue treatment member 300 is 22-mm, the system 100 may be used during PV isolation treatment to form an annular area of ablated tissue along an ostium having a diameter of 20-mm, 30-mm, 40-mm, or greater. A physician is not required to use a larger size of tissue treatment member 300 in order to treat tissue in a relatively larger-sized ostium. Furthermore, because the anchor balloon 210 can be secured at various depths in the pulmonary vein 405, the tissue treatment member 300 can be directed to the desired ostium location even if the ostium is of a relatively small or relatively large size.

Figure 3:
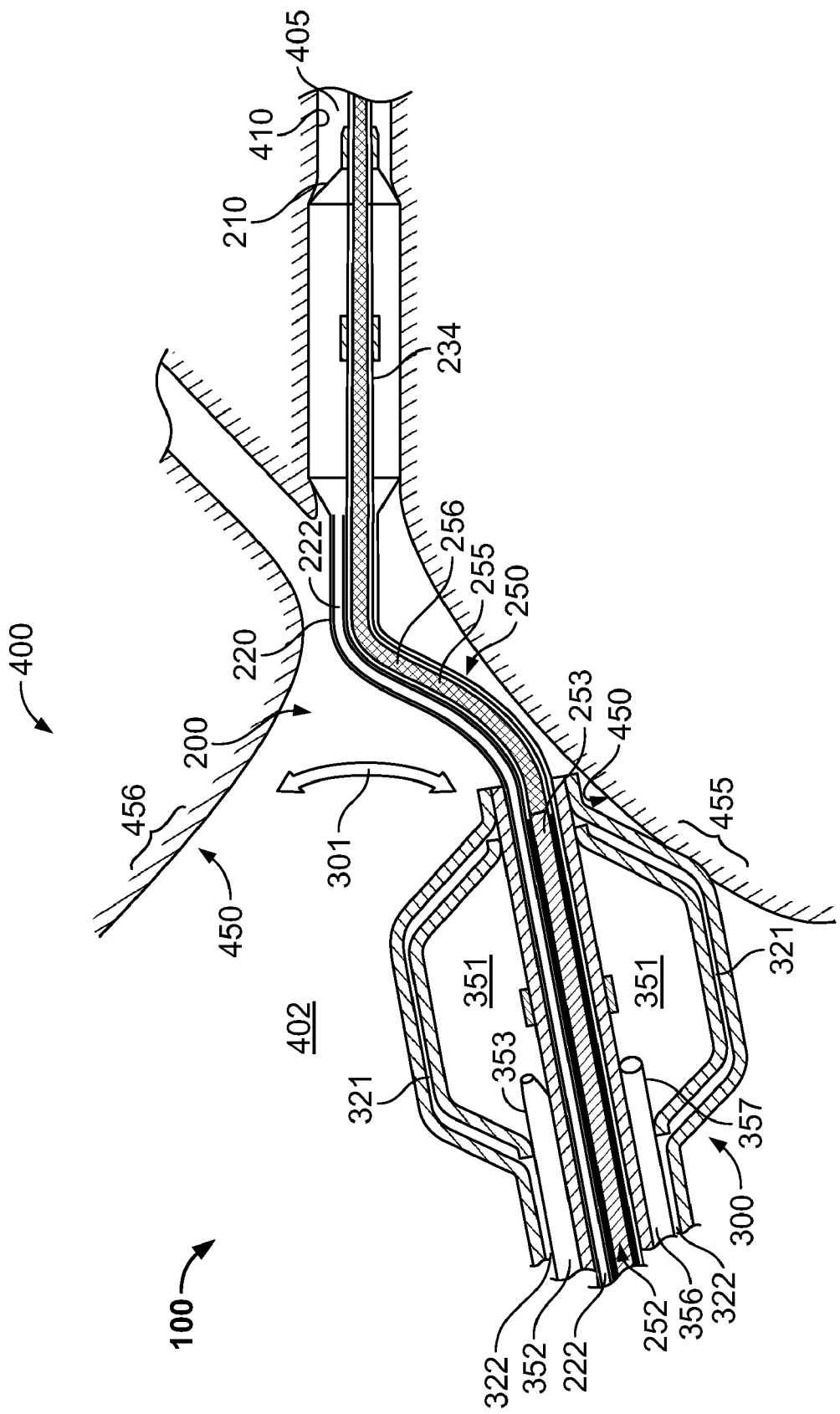
FIG. 3 is a cross-sectional view of a portion of the system of FIG. 1 disposed in the heart.

Referring now to FIG. 3, the anchor balloon 210 of the anchor device 200 may be configured to fit inside a vessel, such as a pulmonary vein 405, and expand to a desired shape to press against a wall 410 of the vessel. In this embodiment, the steerable portion 250 is disposed between the tissue treatment member 300 and the anchor balloon 210. As such, the tissue treatment member 300 may be disposed outside of the pulmonary vein 405 and biased against an area 455 of the ostium 450. When the coolant is cycled into the chamber 351, heat transfer may occur between the contacted ostial area 455 and the tissue treatment member 300. Such heat transfer may cause ablation of tissue cells proximate the ostial area 455 in the left atrium 402. In cases in which the tissue treatment member 300 is not large enough to contact the entire ostium 450, the system's steerable portion 250 may provide the proper guidance to adjust the tissue treatment member 300 to a second ostial area 456 of the ostium 450 so as to form an annular area of ablated tissue along the ostium 450.

As previously described, the steerable portion 250 may include a shape memory element 255 that includes a pre-formed curved portion 256. The shape memory element 255 may be integral with the guide wire instrument 252, and in some embodiments, the entire length of the guide wire instrument 252 may comprise a shape memory material. Because pre-formed curved portion 256 comprises only a relatively small portion of the guide wire instrument 252, some embodiments may include a guide wire instrument that is not comprised of a shape memory material along its entire length. For example, in the embodiment shown in FIGS. 1 and 3, the guide wire instrument 252 includes a shape memory element 255 that is joined at a distal end of a flexible wire 253 comprising a metal or polymer material.

Still referring to FIG. 3, when the targeted tissue in the first ostial area 455 is sufficiently ablated by the tissue treatment member 300, the physician may apply a torque to the guide wire instrument 252 at the proximal portion 110 (FIG. 1). The torque may be applied, for example, by grasping and rotating the handle member 254 (FIG. 1) at the proximal portion 110. Such action causes the guide wire instrument 252 (including the shape memory element 255 at the distal portion of the instrument 252) to rotate in the guide wire lumen 232 of the anchor device 200. In this embodiment, rotation of the shape memory element 255 causes the tissue treatment member 300 to shift with a substantially annular motion 301 relative to the anchor member 210 (e.g., anchor balloon). As such, the steerable portion 250 can provide the proper guidance to adjust the tissue treatment member 300 relative to the anchor member 210 to form an annular area of ablated tissue along the ostium 450. In many cases, the annular area may be formed using one to five cryo lesion ablations, and sometimes only one to three cryo lesion ablations, from the tissue treatment member 300. Such cryo lesion ablations, for example, can be formed by contacting the tissue treatment member 300 for approximately 30 to 120 seconds, depending on coolant material in the chamber 351, the conditions in the patient's body, and other factors.

By forming an annular area of ablated tissue along the ostium 450 (rather than inside the pulmonary vein 405), the catheter ablation therapy may be more effective in treating atrial fibrillation. The annular area of ablated tissue may form an annular scar along the ostium 450, thereby creating a conduction block to stop passage of irregular impulses from within the pulmonary veins to the heart wall. Furthermore, because the steerable portion 250 can be used to adjust the tissue treatment member 300 relative to the anchor member 210, the tissue treatment member 300 may form an annular area of ablated tissue along an outer portion of the ostium 450 known as the antrum. It is believed that, in some cases, forming an annular scar along the antrum is more effective in preventing future occurrences of atrial fibrillation. Some embodiments of the system 100 permit adjustment of the tissue treatment member 300 to form such an annular area of ablated tissue along the antrum even if the antrum is substantially larger than the tissue treatment member 300.

In operation, the system 100 may be directed to the targeted internal body tissue in stages. For example, the anchor device 200 may be directed to a location proximate the targeted tissue, such as through the left atrium and inside the pulmonary vein, before the tissue treatment member 300 is guided over the anchor catheter 220. Alternatively, the tissue treatment member 300 may be directed to a location proximate the targeted tissue, such as inside the left atrium, before the anchor device 200 is guided through the guide lumen 312 of the tissue treatment member 300 toward the pulmonary vein.

Figure 4:
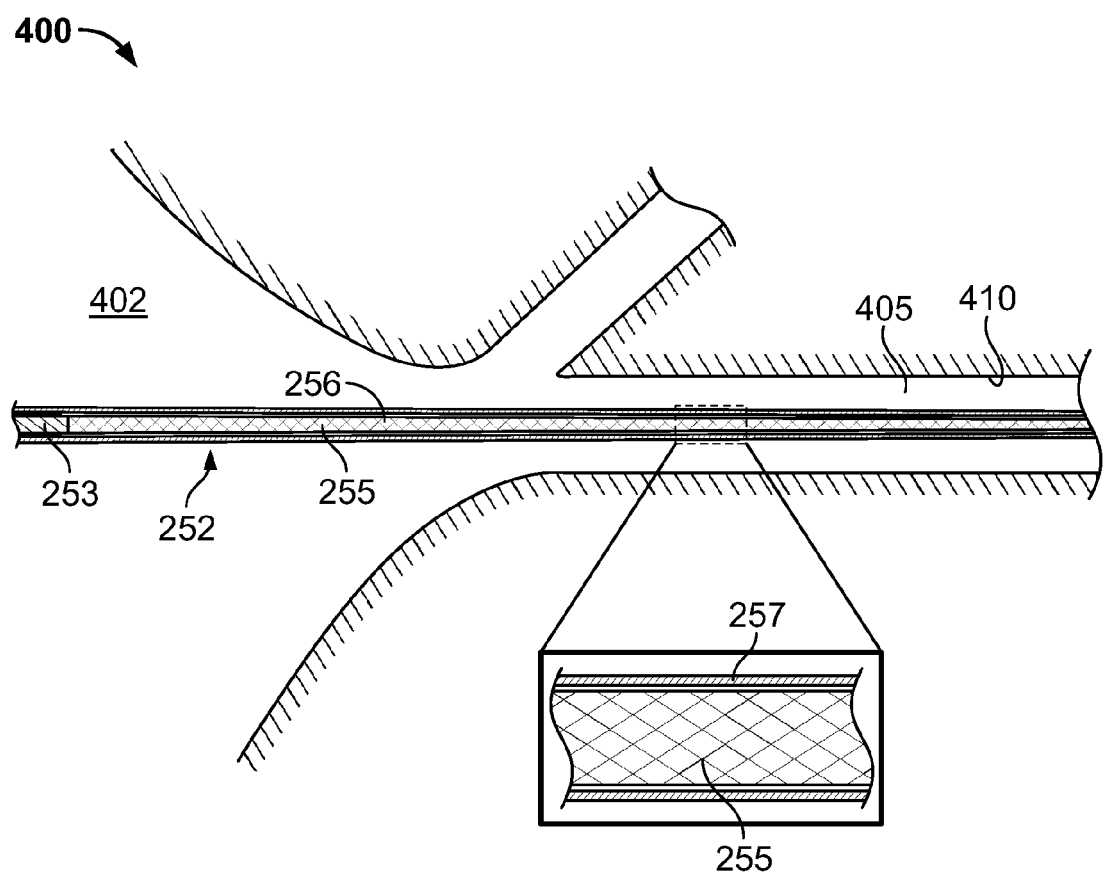
FIG. 4 is a cross-sectional view of certain components of a system proximal to heart tissue.

Referring to FIG. 4, some embodiments of the system 100 may include a guide wire instrument 252 that is directed from a proximal portion 110 outside of the patient's body to a location proximate the targeted tissue, such as through the left atrium 402 and into the pulmonary vein 405. In these embodiments, the guide wire instrument 252 may provide guidance for other instruments that are subsequently directed toward the targeted tissue. In certain embodiments, the guide wire instrument 252 may include an atraumatic tip or a soft, flexible portion at its distal end. Such a tip may facilitate steering and guiding of the guide wire instrument 252 through the various vessels inside the patient's body. For example, the guide wire instrument 252 may be directed from a vein in the patient's leg toward the heart 400, where the guide wire instrument 252 passes from the right atrium, through the atrial septum, and into the left atrium 404.

As previously described, the guide wire instrument may include a shape memory element 255. The shape memory element 255 may extend along the entire length of the guide wire instrument or, as shown in FIG. 4, may extend from a distal end of a flexible wire 253 comprising a metal or polymer material. The shape memory element 255 includes a pre-formed curved portion 256 that may be constrained to a substantially straightened shape during guidance of the guide wire instrument 252 through the body. For example, the curved portion 256 may be disposed in a thin-walled sheath 257, such as a hypotube, to constrain the shape memory element 255 into a substantially straightened shape. The sheath 257 may be slidably engaged with at least a portion of shape memory element 255 such that the sheath may retract in a proximal direction away from the curved portion 256 when the guide wire instrument 252 reaches the desired location in the patient's body. The retraction of the sheath 257 may be control by a physician at the proximal portion 110 (FIG. 1) of the system 100.

Figure 5:
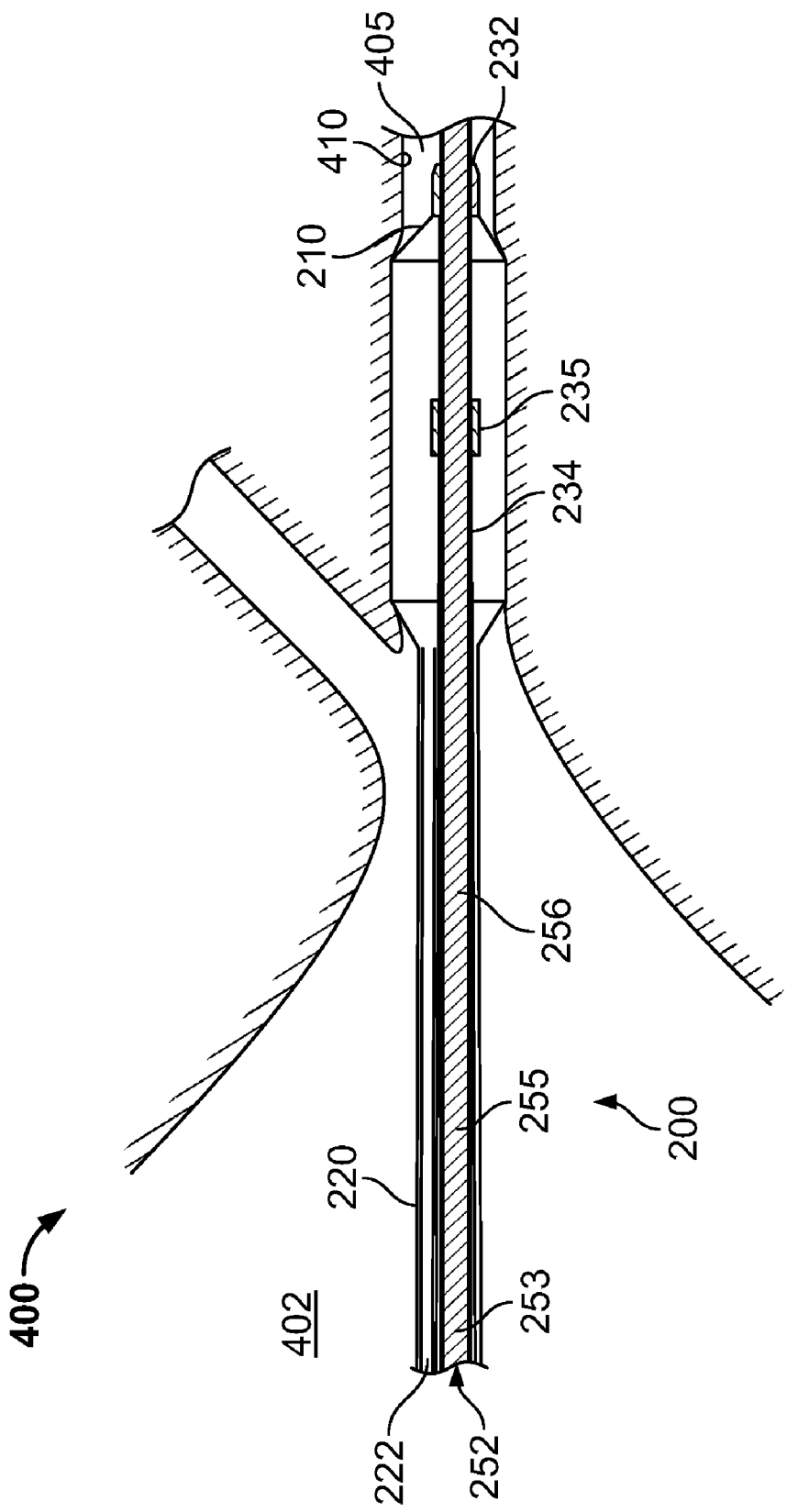
FIG. 5 is a cross-sectional view of certain components of the system of FIG. 4.

Referring now to FIG. 5, the anchor device 200 may be directed over the guide wire instrument 252 toward the desired location, such as the pulmonary vein 405. As previously described, the anchor device 200 includes a guide wire lumen 232 through which the guide wire instrument 252 may pass. At the proximal portion 110 (FIG. 1), the tubular wall 234 of the guide wire lumen 232 may be directed over the guide wire instrument 252. From there, the anchor device 200 may be forced to slide over the guide wire instrument 252 through the left atrium 402 and into the pulmonary vein 405. In some embodiments, the sheath 257 (FIG. 4) may remain over the curved portion 256 until after the anchor member 210 is guided into the pulmonary vein 405. The marker band 235 may be used to visualized the location of the anchor member 210 in the pulmonary vein 405. When the anchor member 210 is properly positioned in the pulmonary vein 405, the pressure source 224 (FIG. 1) may deliver pressurized fluid (e.g., saline solution) through the inflation lumen 222 to expand the anchor balloon 210. In this embodiment, the anchor member 210 includes an expandable balloon. When expanded to its pressurized shape, the anchor balloon 210 presses against the wall 410 of the pulmonary vein 405 to secure its position in the pulmonary vein 405.

Figure 6:
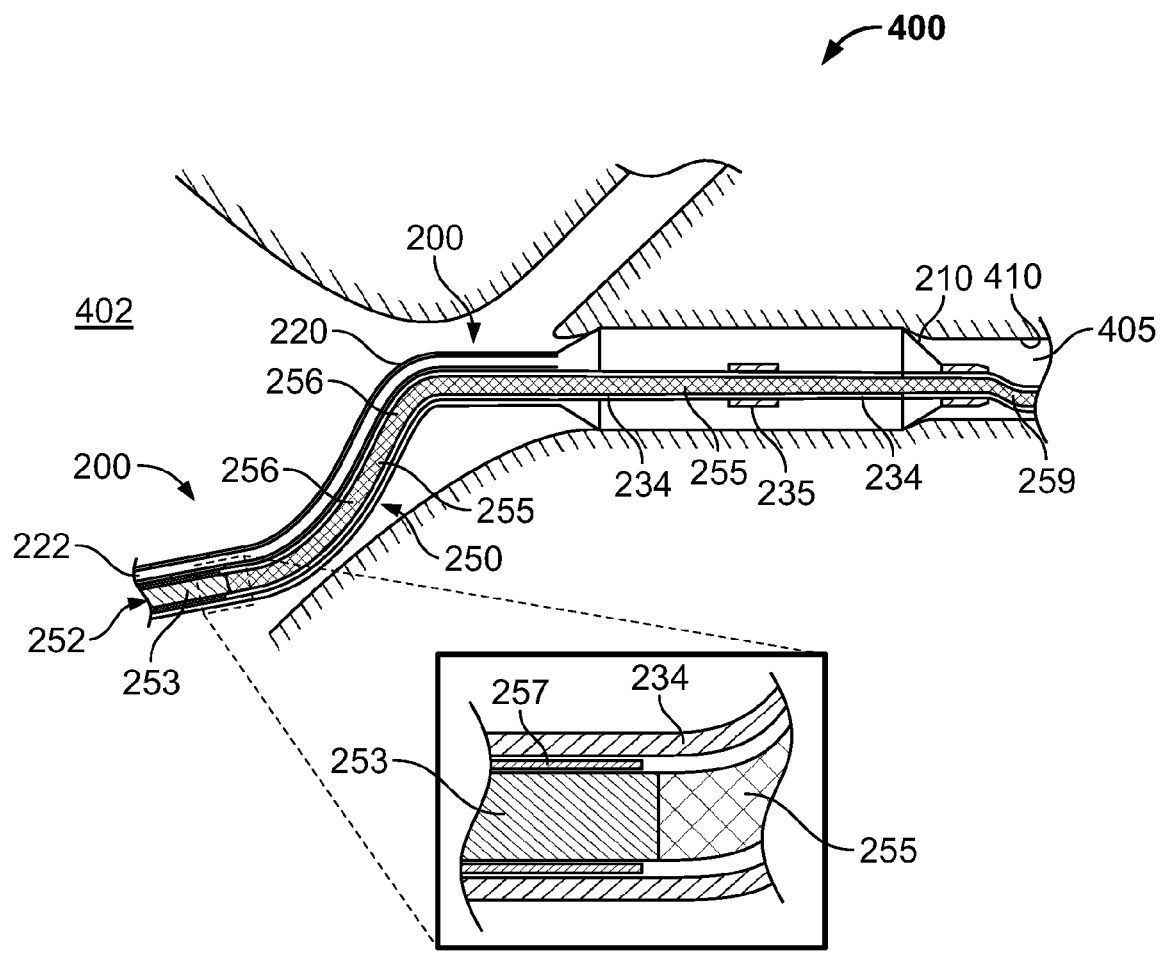
FIG. 6 is a cross-sectional view of certain components of the system of FIG. 4.

Referring to FIG. 6, when the anchor device 200 is properly secured in the pulmonary vein 405, the sheath 257 may be retracted from the curved portion 256 of the shape memory element 255. The shape memory element 255 may then return to its pre-formed curved shape when no longer constrained by the sheath 257. The sheath 257 need only be retracted to a position that permits the curved portion 256 to return to its biased shape. In this embodiment, the sheath 257 is retracted to a position over the flexible wire 253 and just proximal of the shape memory element 255. At least a portion of the sheath 257 that extends over the curved portion 256 may be rigid enough to constrain the shape memory element 255. The portions of the tubular wall 234 and the anchor catheter 220 that are disposed over the curved portion 256 may be substantially less rigid than the rigid portion of the sheath 257. As such, those portions of the tubular wall 234 and the catheter 220 deform to one or more curves that are somewhat similar to the curved portion 256.

In some embodiments, the shape memory element 255 may also include a second curved portion 259 that is generally distal of the anchor balloon 210. The second curved portion 259 may curved away from the distal opening of the tubular wall 234 when the sheath 257 no longer constrains the second curved portion 259. In these embodiments, the second curved portion 259 may serve to hinder the guide wire instrument 252 (including the shape memory element 255) from shifting in a proximal direction relative to the anchoring balloon 210. In other embodiments, the distal end of the guide wire instrument 252 may include a distal tip that is larger than the distal opening of the tubular wall 234 so that the distal tip is prevented from shifting proximally relative to the anchoring balloon 210. Alternatively, the guide wire instrument 252 may remain in slidable engagement with the tubular wall 234 such that the distal end of the guide wire instrument 252 is permitted to shift in a proximal or distal direction relative to the anchoring balloon 210.

Figure 7:
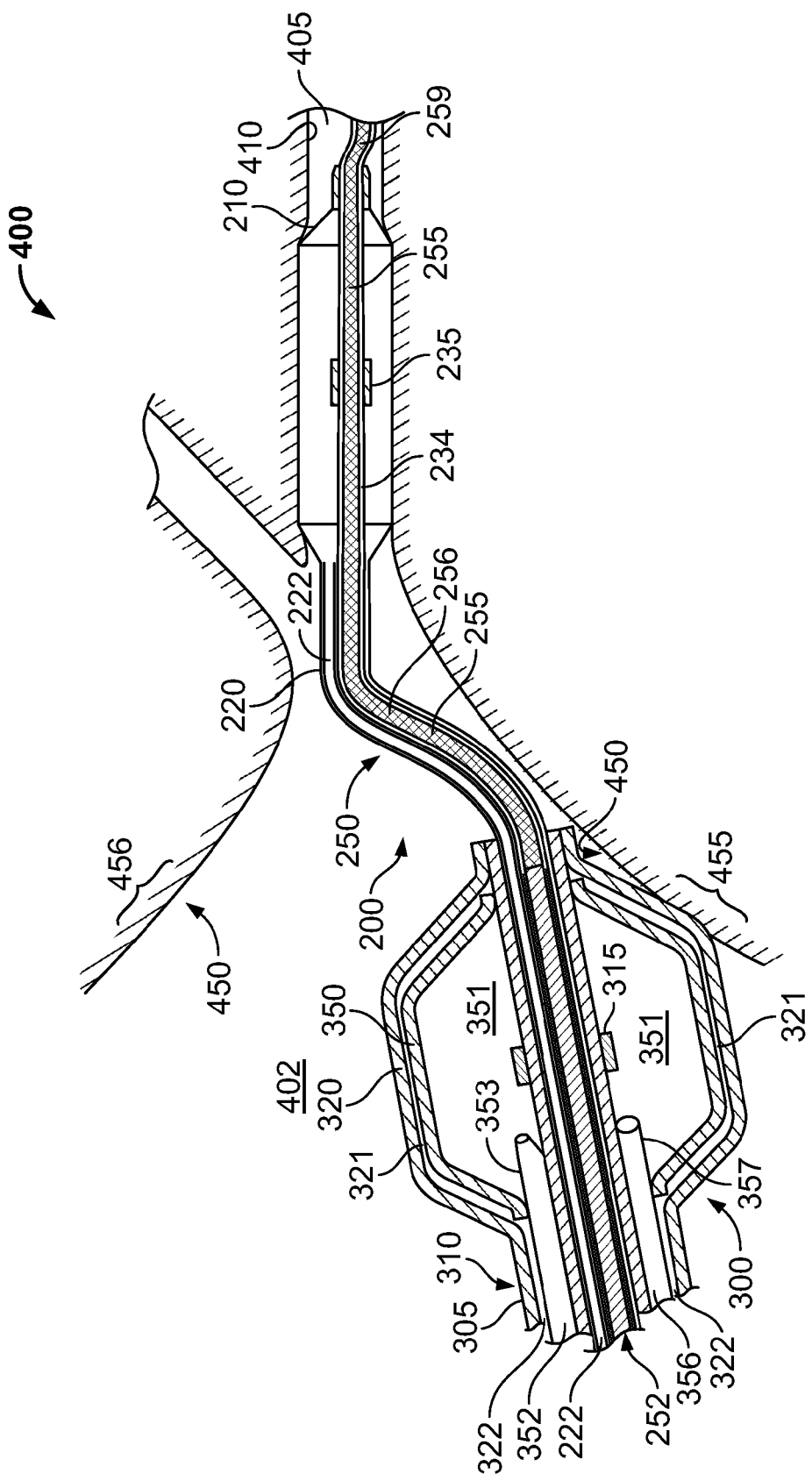
FIG. 7 is a cross-sectional view of certain components of the system of FIG. 4.

Referring to FIG. 7, the tissue treatment member 300 may be directed over the outer surface of the anchor catheter 220 toward the desired location, such as the left atrium 402. The curved portion 256 of the shape memory element 255 may bias the anchor catheter 220 toward an ostial area 455 in the left atrium 402. When the tissue treatment member 300 approaches the steerable portion 250 of the system 100, the tissue treatment member 300 may be guided proximate to the ostial area 455. The position of the tissue treatment member 300 may be visualized by a physician using the marker band 315 and known imaging techniques. After the tissue treatment member 300 is guided to the proper position, the coolant material may be cycled through the coolant chamber 351 (e.g., through intake and exhaust tubes 353 and 357) while a vacuum is applied to the safety chamber 321. The tissue treatment member 300 may be directed over the anchor catheter 210 (and the guide wire instrument 252 therein) so as to contact the ostial area 455. For example, a physician may grasp an outer surface 305 of the elongate member 310 (or a handle member attached thereto) at the proximal portion 110 (FIG. 1) of the system 100 and then force the tissue treatment member 300 to press against the ostial area 455. The heat transfer that occurs between the ostial area 455 and the tissue treatment member 300 may cause ablation of the tissue proximate the ostial area 455.

As previously described in connection with FIG. 3, when the targeted tissue in the first ostial area 455 is sufficiently ablated by the tissue treatment member 300, the physician may apply a torque to the guide wire instrument 252 at the proximal portion 110 (FIG. 1). Such action causes the guide wire instrument 252 (including the shape memory element 255 at the distal portion of the instrument 252) to rotate in the guide wire lumen 232 of the anchor device 200, which may cause the tissue treatment member 300 to shift with a substantially annular motion relative to the anchor member 210. As such, the steerable portion 250 can provide the proper guidance to adjust the tissue treatment member 300 relative to the anchor member 210 to form an annular area of ablated tissue along the ostium 450. Forming an annular area of ablated tissue along the ostium 450 (rather than inside the pulmonary vein 405) may be more effective at treating atrial fibrillation. Furthermore, because the steerable portion 250 can be used to adjust the tissue treatment member 300 relative to the anchor member 210, the tissue treatment member 300 may form an annular area of ablated tissue along an outer portion of the ostium 450 known as the antrum. It is believed that, in some cases, forming an annular scar along this outer ostial area known as the antrum is more effective in preventing future occurrences of atrial fibrillation.

Figure 8:
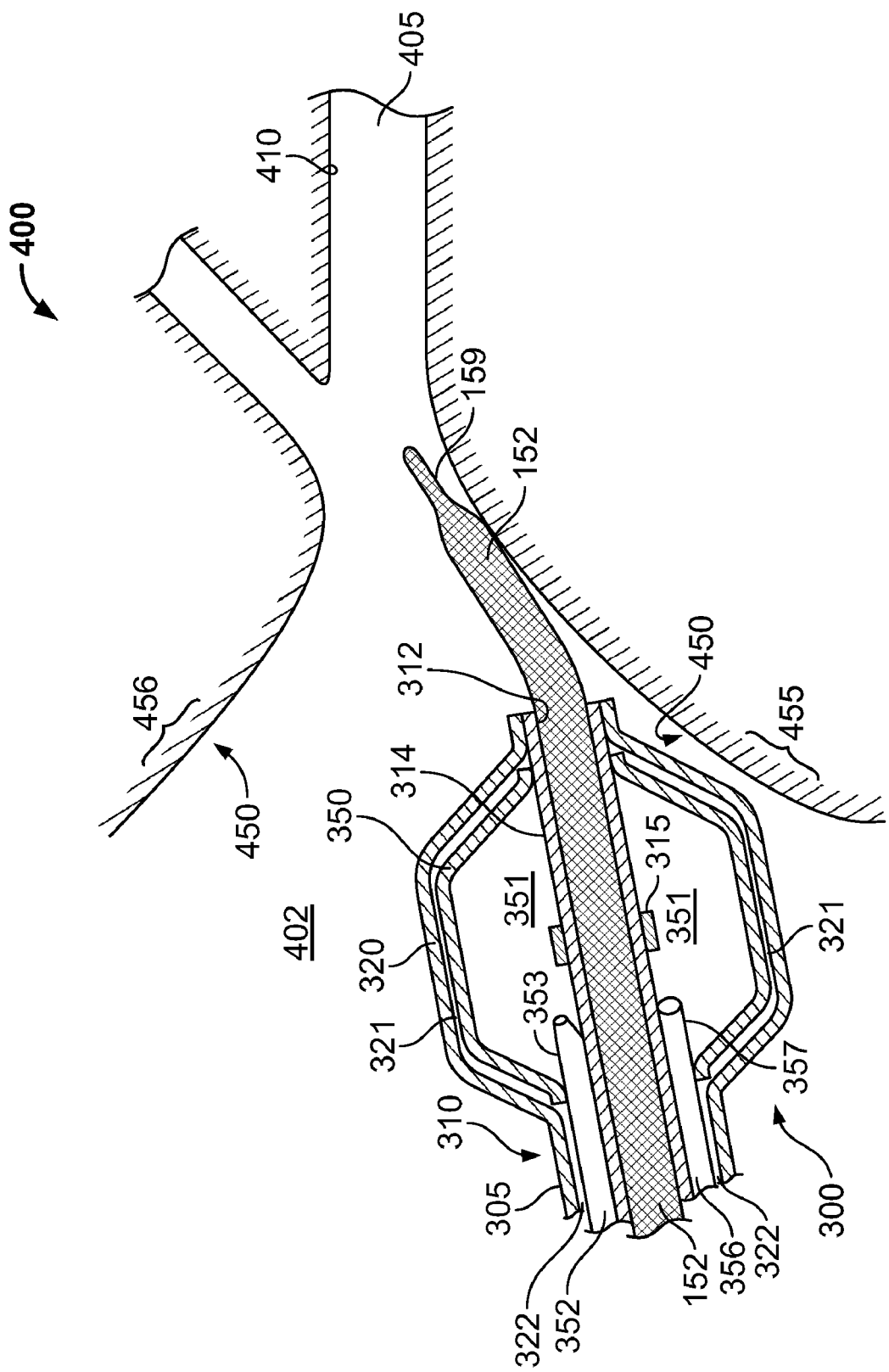
FIG. 8 is a cross-sectional view of certain components of a system proximal to heart tissue.
Figure 9:
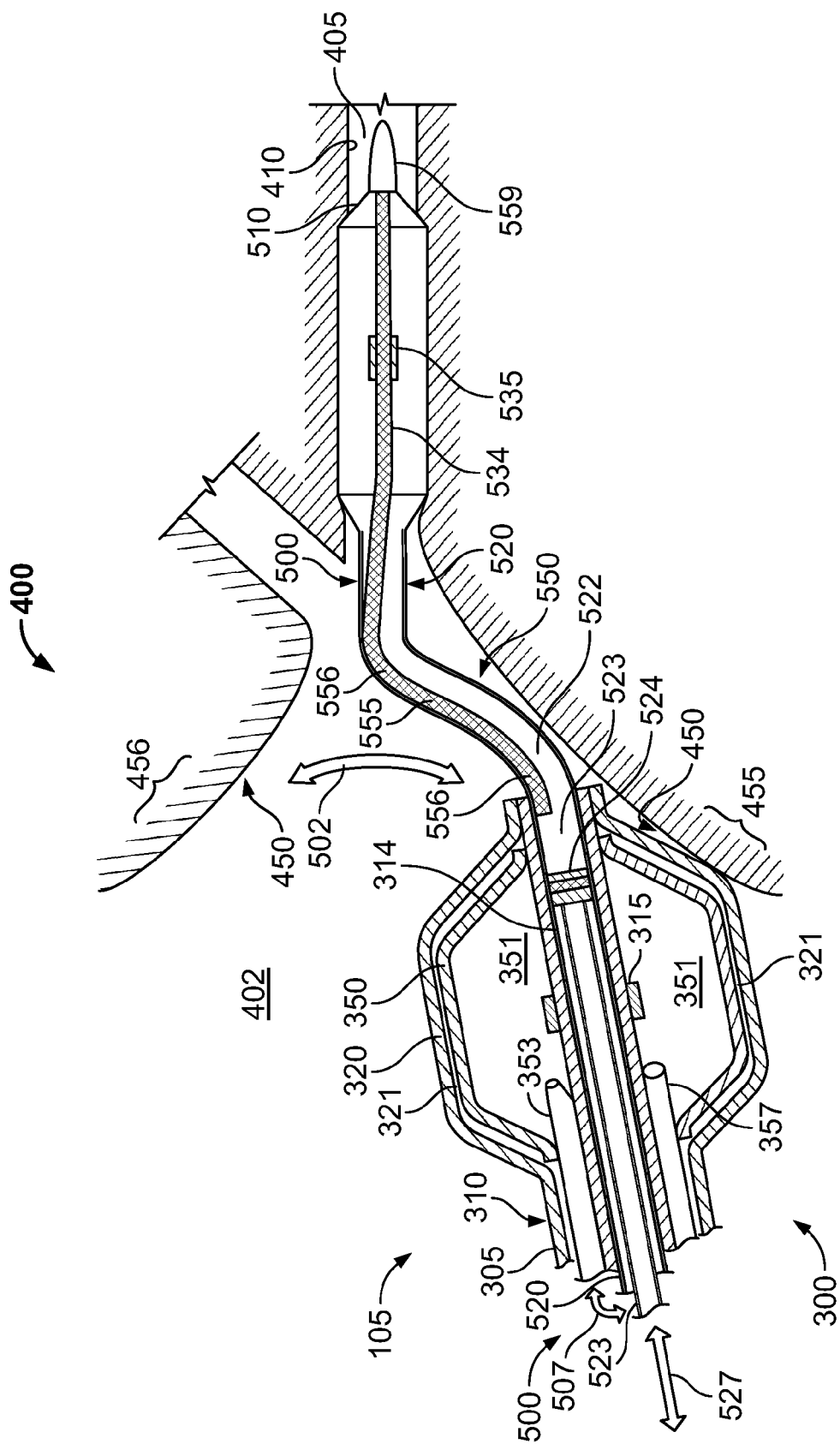
FIG. 9 is a cross-sectional view of certain components of the system of FIG. 8.

Referring now to FIGS. 8-9, some embodiments of the system may include a tissue treatment member 300 that is delivered to the desired location inside the patient's body before the anchor device. In such embodiments, the anchor device may pass through the guide lumen 312 of the tissue treatment member 300. Also in such embodiments, the steerable portion may be coupled to the anchor device, which may eliminate the need for the guide wire instrument that passes through the anchor device. The steerable portion that is coupled to the anchor device can provide guidance to annularly adjust the tissue treatment member 300 relative to the anchor member (e.g., an expandable balloon structure).

Referring to FIG. 8, a steerable guide wire 152 may be directed to the left atrium 402 using known techniques. The guide wire 152 may include an atraumatic tip 159 to facilitate the steering and guidance of the wire 152 through the patient's body. The guide wire 152 may be sized to slidably engage the guide lumen 312 of the tissue treatment member 300. The tissue treatment member 300 may be directed to the left atrium 402 by sliding the tubular wall 314 of the guide lumen over the outer surface of the guide wire 152. (The coolant chamber 351 and the safety chamber 321 are shown in expanded states for illustrative purposes, and it should be understood that the chambers 321 and 351 are not expanded while being guided through the patient's body.) After the tissue treatment member is guided to the desired location in the left atrium, the guide wire 152 may be removed by sliding the wire 152 out through guide lumen 312 to a proximal portion (located outside the patient's body like the proximal portion 110 shown in FIG. 1) of the system.

Referring to FIG. 9, some embodiments of the anchor device 500 include an anchor member 210 disposed at a distal end of an anchor catheter 520. The anchor member 510 may include an expandable balloon structure. In such embodiments, the anchor catheter 520 may extend from the anchor balloon 510 proximally back to the proximal portion of the system 105 located outside the patient's body—similar to embodiments of catheter devices described in U.S. Pat. No. 5,545,133 to Burns et al, which is incorporated herein by reference. The anchor member 500 may be sized to slidably engage the guide lumen 312 of the tissue treatment member 300. Also, a steerable portion 550 may be coupled to the anchor device 500 proximate to the balloon 510. The steerable portion 550 that is coupled to the anchor device 500 can provide guidance to annularly adjust the tissue treatment member 300 relative to the anchor balloon 510.

In the embodiment shown in FIG. 9, the steerable portion 550 includes a shape memory element 555 that may be preformed to have a curved portion 556 such that when the catheter 520 (coupled to the shape memory element 555) is rotated, the tissue treatment member 300 is adjusted annularly relative to the anchor balloon 510. As previously described, the pre-formed shape memory element 555 may comprise a superelastic Nitinol material that was exposed to austenitic/martensite processing. The shape memory element 555 may also comprise multiple wires that can be made to shorten under application of electrical current. In such embodiments, the multiple wires may be positioned along the periphery of the anchor catheter 520 with each wire being spaced apart from the neighboring wire. In other embodiments, the steerable portion 550 may include various mechanisms to adjust the position of the tissue treatment member 300 relative to the anchor balloon 510. For example, the steerable portion 550 may include one or more pull wires that are operated at the proximal portion of the system 105 to control the position of the tissue treatment member 300 relative to the anchor balloon 510.

Still referring to FIG. 9, while the tubular wall 314 in the elongate member 310 and the tissue treatment member 300 may be sufficiently rigid to constrain the shape memory element 555, the portion of the anchor catheter 520 that contains the curved portion 556 may be less rigid. As such, when the anchor device 500 is directed through the guide lumen 312 toward the left atrium 402, the curved portion 556 of the shape memory element 555 may be constrained by the tubular wall 314 of the guide lumen 312. However, when a portion of the anchor device 500 extends distally from the tissue treatment member 300 such that the curved portion 556 is no longer inside the tubular wall 314, the shape memory element 555 returns to its biased, curved shape.

In some embodiments, the nonexpanded tissue treatment member 300 may be guided adjacent to the pulmonary vein 405 so that the anchor balloon 510 may be guided directly into the vein 405 and expanded to press against the vein wall 410. Then, the tissue treatment member 300 may be slightly retracted in the proximal direction while the anchor balloon 510 remains in the pulmonary vein 405 such that the curved portion 556 of the shape memory element 555 extends distally of the tissue treatment member 300. The anchor device 500 may include an atraumatic tip 559 that is relatively flexible to facilitate the guidance of the anchor balloon 510 into the pulmonary vein 405.

In the embodiment shown in FIG. 9, the anchor member 500 includes a piston 524 that is disposed inside a chamber 523. The piston 524 may act as a pressure source that forces fluid to inflate or deflate the anchor balloon 510. A physician may apply a longitudinal force 527 to the piston 524, which causes the inflation fluid (e.g., saline solution) to enter or withdraw from the anchor balloon 510. The piston 524 may be located near the distal portion of the system 105 and may be actuated at the proximate portion of the system 105—similar to embodiments described in the previously referenced U.S. Pat. No. 5,545,133 to Burns et al. In such circumstances where the pressure source is located closer to the anchor balloon 510 (rather than at the proximate portion outside the patient's body), the length of the inflation lumen 522 is reduced. The shortened inflation lumen 522 reduces both the resistance to fluid flow and may reduce the time required to inflate and deflate the anchor balloon 510.

Still referring to FIG. 9, the tissue treatment member 300 forced into a position proximate an ostial area 455 due to the bias from the shape memory element 555 (and any pushing force applied to the elongated member 310 from a physician at the proximal portion of the system 105). The position of the tissue treatment member 300 may be visualized by a physician using the marker band 315 and known imaging techniques. After the tissue treatment member 300 is guided to the proper position, the coolant material may be cycled through the coolant chamber 351 (e.g., through intake and exhaust tubes 353 and 357) while a vacuum is applied to the safety chamber 321. The tissue treatment member 300 may be directed over the outer surface of the anchor catheter 520 so as to contact the ostial area 455. For example, a physician may grasp an outer surface 305 of the elongate member 310 (or a handle attached thereto) at the proximal portion of the system 105 so as to force the tissue treatment member 300 to press against the ostial area 455. The heat transfer that occurs between the ostial area 455 and the tissue treatment member 300 may cause ablation of the tissue proximate the ostial area 455.

When the targeted tissue in the first ostial area 455 is sufficiently ablated by the tissue treatment member 300, the physician may apply a torque 507 to anchor catheter 520 at the proximal portion of the system. Such action causes the anchor catheter 520 (including the shape memory element 255 at the steerable portion 250) to rotate relative to the pulmonary vein 405. Optionally, if the anchor balloon 510 presses against the vein wall 410 to a force that is sufficient to prevent rotation of the catheter 520, the balloon 510 may be partially deflated while the catheter 520 is rotated and then reinflated. Rotation of the catheter 520 relative to the pulmonary vein 405 may cause the tissue treatment member 300 to shift with a substantially annular motion 502 relative to the position of the anchor balloon 510 in the pulmonary vein 405. From there, the tissue treatment member 300 may be used to ablate tissue proximate a second ostial area 456. As such, the steerable portion 250 can provide the proper guidance to adjust the tissue treatment member 300 relative to relative to the position of the anchor balloon 510 in the pulmonary vein 405 so at to form an annular area of ablated tissue along the ostium 450.

As previously described, forming an annular area of ablated tissue along the ostium 450 (rather than inside the pulmonary vein 405) may be more effective at treating atrial fibrillation. Furthermore, because the steerable portion 250 can be used to annularly adjust the tissue treatment member 300 relative to the position of the anchor balloon 510 in the pulmonary vein 405, the tissue treatment member 300 may form an annular area of ablated tissue along an outer portion of the ostium 450 known as the antrum. It is believed that, in some cases, forming an annular scar along this outer ostial area known as the antrum is more effective in preventing future occurrences of atrial fibrillation.

While the embodiments depicted in FIGS. 1-9 include an anchor member having an expandable balloon, other devices may be used to stabilize the steerable portion relative to the vein. For example, a guide wire instrument may include an ostial curved portion (similar to the curved portion 256 described above) and a distal curved portion that is sized to press against the pulmonary vein wall. When the distal curved portion is in the pulmonary vein, the tissue treatment member 300 may be directed over the guide wire instrument toward the ostium, where the ostial curved portion biases the tissue treatment member 300 against an ostial area. The distal curved portion may replace the need for an anchor balloon, as it would press against a vein wall and help to stabilize the position of the ostial curved portion relative to the ostium. The anchor member may also take other appropriate forms, including an expandable stent structure or an expandable ring. The expandable stent structure or the expandable ring may be used to stabilize the steerable portion relative to the vein, and may be controlled by one or more pull wires that extend to the proximal portion of the system. In another example, the anchor member may comprise an expandable wire structure, such as medically safe filter wire. The filter wire structure may be a FilterWire EX™ system provided by Boston Scientific Corporation. The filter wire may include a shape memory element that causes the filter wire structure to selectively expand when in the pulmonary vein so that the anchor member is secured to a targeted portion of the pulmonary vein.

Additionally, in embodiments where the steerable portion uses a shape memory element, the shape memory element is not necessarily a pre-formed wire. For example, the shape memory element may be a tube that slides over an anchor catheter. The shape memory tube may have a curved portion that is similar to the curved portion 256 described above. In such embodiments, the shape memory tube may extend distally from the tissue treatment member 300. When the shape memory tube is advanced over a flexible portion of the anchor catheter (after the anchor balloon is secured in the pulmonary vein), the anchor catheter is flexed and the shape memory tube biases the tissue treatment member 300 against an ostial surface. In these embodiments, the use of the pre-formed tube having the curved portion may be used as a treatment option in cases where the physician desires to annularly adjust the tissue treatment member relative to the anchor balloon in the pulmonary vein.

Other embodiments of the system may include a tissue treatment member having a different shape. The external and internal balloons of the tissue treatment member are not necessarily spherical, but instead may be cylindrically shaped, tear-drop shaped, prism shaped, or other shapes depending on the tissue surface, geometry that is to be treated, and other factors.

In some embodiments, the tissue treatment member 300 may include a single balloon construction, in which the external balloon 320 and the vacuum lumen 322 are not necessarily included. In these embodiments, the non-expanded size of the tissue treatment member 300 may be reduced.

Furthermore, some embodiments of the tissue treatment member do not necessarily require expandable balloons. The coolant chamber may be disposed in a substantially nonexpandable container that is adjustable relative to the anchor balloon so as to contact ostial areas. For example, the tissue treatment member may include a nonexpandable container having an outer cylindrical surface and a central guide lumen passing therethrough. When coolant cycles through the coolant chamber in the nonexpandable container, the outer cylindrical surface may be pressed against ostial areas to form an annular area of ablated tissue.

A number of embodiments of the invention have been described. Nevertheless, it will be understood that various modifications may be made without departing from the spirit and scope of the invention. Accordingly, other embodiments are within the scope of the following claims.

What is claimed is:

1. A system to treat tissue internal to a body, comprising:
   an elongate member having a proximal portion and a distal portion, the elongate member including a plurality of lumens extending therethrough;
   a tissue treatment member disposed at the distal portion of the elongate member, the tissue treatment member being in fluid communication with at least one of the lumens of the elongate member, and the elongate member having a continuous outer surface extending to the tissue treatment member; and
   an anchor member adjustably engaged with the tissue treatment member such that, when the anchor member extends from an opening in a distal end of the tissue treatment member and is disposed in a position at least partially in a pulmonary vein, the tissue treatment member is nonaligned with the anchor member and is annularly adjustable relative to the position of the anchor member from a first annular position in contact with a first ostial area to a second annular position in contact with a second ostial area.

2. The system of claim 1, wherein the tissue treatment member is operable to ablate tissue that contacts an outer surface of the tissue treatment member.

3. The system of claim 1, further comprising a second elongate member that is coupled to the anchor member, the second elongate member and the anchor member being passable through a guide lumen that extends through the first elongate member and the tissue treatment member so that the anchor member extends from the opening in the distal end of the tissue treatment member.

4. The system of claim 1, wherein the anchor member comprises an expandable anchor balloon having an outer surface to press against a vein wall.

5. The system of claim 1, wherein the tissue treatment member comprises an expandable ablation balloon that is nonelastically inflatable to a fixed size and is substantially nondeformable beyond the fixed size.

6. The system of claim 5, wherein the expandable ablation balloon defines a coolant chamber in which a cryo coolant is cycled, the coolant chamber being in fluid communication with at least one coolant lumen that extends through the first elongate member.

7. The system of claim 5, wherein the expandable ablation balloon defines an inflation chamber to receive a chemical solution, further comprising electrodes disposed in the inflation chamber to heat the chemical solution using RF energy.

8. A system to treat tissue internal to a body, comprising:
   an elongate member having a proximal portion and a distal portion, the elongate member including at least one lumen extending therethrough;
   a tissue treatment member disposed at the distal portion of the elongate member, the tissue treatment member being in fluid communication with the lumen; and
   an anchor member adjustably engaged with the tissue treatment member such that, when the anchor member extends from an opening in a distal end of the tissue treatment member and is disposed in a position at least partially in a pulmonary vein, the tissue treatment member is nonaligned with the anchor member and is annularly adjustable relative to the position of the anchor member from a first annular position in contact with a first ostial area to a second annular position in contact with a second ostial area,
   wherein the tissue treatment member is operable to ablate tissue that contacts an outer surface of the tissue treatment member, and
   wherein when the anchor member is distally disposed in the position at least partially in the pulmonary vein, the tissue treatment member is adjustable relative to the position of the anchor member so as to form an annular area of ablated tissue along an antrum.

9. The system of claim 8, further comprising a second elongate member that is coupled to the anchor member, the second elongate member and the anchor member being passable through a guide lumen that extends through the first elongate member and the tissue treatment member so that the anchor member extends from the opening in the distal end of the tissue treatment member.

10. The system of claim 9, wherein the anchor member comprises an expandable anchor balloon having an outer surface to press against a vein wall.

11. The system of claim 10, wherein the tissue treatment member comprises an expandable ablation balloon that is nonelastically inflatable to a fixed size and is substantially nondeformable beyond the fixed size.

12. The system of claim 11, wherein the expandable ablation balloon defines a coolant chamber in which a cryo coolant is cycled, the coolant chamber being in fluid communication with at least one coolant lumen that extends through the first elongate member.

13. The system of claim 11, wherein the expandable ablation balloon defines an inflation chamber to receive a chemical solution, further comprising electrodes disposed in the inflation chamber to heat the chemical solution using RF energy.

14. A system to treat tissue internal to a body, comprising:
   an elongate body having at least one lumen extending between a proximal portion and a distal portion;
   a tissue ablation device arranged at the distal portion of the elongate body, the tissue ablation device outputting ablation energy when activated by a user-controlled instrument coupled to the proximal portion of the elongate body; and a pulmonary anchor balloon to be received inside a pulmonary vein and extend distally from a distal end of the tissue ablation device, the pulmonary anchor balloon being axially movable relative to the distal end of the tissue ablation device, wherein when the pulmonary anchor balloon is received in the pulmonary vein, the tissue ablation device is biased away from axial alignment with pulmonary anchor balloon and is annularly adjustable relative to the position of the pulmonary anchor balloon from a first position in contact with a first ostial area to a second position in contact with a second ostial area.

15. The system of claim 14, further comprising an elongate anchor catheter that is coupled to the pulmonary anchor balloon, the elongate anchor catheter and the pulmonary anchor balloon being deliverable through a guide lumen that extends through the elongate body and the distal end of the tissue ablation device.

16. The system of claim 15, wherein the pulmonary anchor balloon extends distally from the distal end of the tissue ablation device when the elongate anchor catheter is delivered through the guide lumen and out of an opening at the distal end of the tissue ablation device.

17. The system of claim 14, further comprising a biasing portion disposed between the tissue ablation device and the pulmonary anchor balloon when the pulmonary anchor balloon is positioned distally of the tissue ablation device, the biasing portion being configured to bias the tissue ablation device away from axial alignment with pulmonary anchor balloon.

18. The system of claim 17, wherein the biasing portion includes a flexible element having a curved portion.

19. The system of claim 14, wherein when the pulmonary anchor balloon is distally disposed inside the pulmonary vein, the tissue ablation device is adjustable relative to the position of the pulmonary anchor balloon so as to form an annular area of ablated tissue along an antrum.

20. The system of claim 19, wherein the tissue ablation device comprises a first expandable balloon.

21. The system of claim 20, wherein the first expandable balloon defines a coolant chamber in which a cryo coolant is cycled, the coolant chamber being in fluid communication with at least one coolant lumen that extends through the elongate body.

22. The system of claim 21, wherein the tissue ablation device comprises a second expandable balloon that substantially surrounds the first expandable balloon to define a safety chamber in fluid communication with a vacuum lumen extending through the elongate body.

23. The system of claim 20, wherein the first expandable balloon defines an inflation chamber to receive a chemical solution, further comprising electrodes arranged along the inflation chamber to heat the chemical solution using RF energy.

24. The system of claim 14, wherein the elongate body comprises a first lumen in fluid communication with the tissue ablation device and a guide lumen extending centrally through the tissue ablation device to a distal opening at the distal end of the tissue ablation device, and wherein an elongate anchor member coupled to the pulmonary anchor balloon is slidably movable within the guide lumen so that elongate anchor member extends from the distal opening at the distal end of the tissue ablation device.

25. A system to treat tissue internal to a body, comprising:
an elongate body having at least one lumen extending between a proximal portion and a distal portion;

a tissue ablation device arranged at the distal portion of the elongate body, the tissue ablation device outputting ablation energy when activated by a user-controlled instrument coupled to the proximal portion of the elongate body;

a pulmonary anchor balloon to be received inside a pulmonary vein and extend distally from a distal end of the tissue ablation device; and an elongate anchor catheter that is coupled to the pulmonary anchor balloon, the elongate anchor catheter and the pulmonary anchor balloon being deliverable through a guide lumen that extends through the elongate body and the distal end of the tissue ablation device, wherein when the pulmonary anchor balloon is received in the pulmonary vein, the tissue ablation device is biased away from axial alignment with pulmonary anchor balloon and is annularly adjustable relative to the position of the pulmonary anchor balloon from a first position in contact with a first ostial area to a second position in contact with a second ostial area.

26. The system of claim 25, wherein the pulmonary anchor balloon extends distally from the distal end of the tissue ablation device when the elongate anchor catheter is delivered through the guide lumen and out of an opening at the distal end of the tissue ablation device.

27. The system of claim 25, further comprising a biasing portion disposed between the tissue ablation device and the pulmonary anchor balloon when the pulmonary anchor balloon is positioned distally of the tissue ablation device, the biasing portion being configured to bias the tissue ablation device away from axial alignment with pulmonary anchor balloon.

28. The system of claim 27, wherein the biasing portion includes a flexible element having a curved portion.

29. The system of claim 25, wherein when the pulmonary anchor balloon is distally disposed inside the pulmonary vein, the tissue ablation device is adjustable relative to the position of the pulmonary anchor balloon so as to form an annular area of ablated tissue along an antrum.

30. The system of claim 29, wherein the tissue ablation device comprises a first expandable balloon.

31. The system of claim 30, wherein the first expandable balloon defines a coolant chamber in which a cryo coolant is cycled, the coolant chamber being in fluid communication with at least one coolant lumen that extends through the elongate body.

32. The system of claim 31, wherein the tissue ablation device comprises a second expandable balloon that substantially surrounds the first expandable balloon to define a safety chamber in fluid communication with a vacuum lumen extending through the elongate body.

33. The system of claim 30, wherein the first expandable balloon defines an inflation chamber to receive a chemical solution, further comprising electrodes arranged along the inflation chamber to heat the chemical solution using RF energy.

34. The system of claim 25, wherein the elongate body comprises a first lumen in fluid communication with the tissue ablation device and a guide lumen extending centrally through the tissue ablation device to a distal opening at the distal end of the tissue ablation device, and wherein an elongate anchor member coupled to the pulmonary anchor balloon is slidably movable within the guide lumen so that elongate anchor member extends from the distal opening at the distal end of the tissue ablation device.

35. A system to treat tissue internal to a body, comprising:
an elongate body having at least one lumen extending between a proximal portion and a distal portion;
a tissue ablation device arranged at the distal portion of the elongate body, the tissue ablation device outputting ablation energy when activated by a user-controlled instrument coupled to the proximal portion of the elongate body;
a pulmonary anchor balloon to be received inside a pulmonary vein and extend distally from a distal end of the tissue ablation device; and
a biasing portion disposed between the tissue ablation device and the pulmonary anchor balloon when the pulmonary anchor balloon is positioned distally of the tissue ablation device, the biasing portion being configured to bias the tissue ablation device away from axial alignment with pulmonary anchor balloon,
wherein when the pulmonary anchor balloon is received in the pulmonary vein, the tissue ablation device is biased away from axial alignment with pulmonary anchor balloon and is annularly adjustable relative to the position of the pulmonary anchor balloon from a first position in contact with a first ostial area to a second position in contact with a second ostial area.

36. The system of claim 35, wherein the biasing portion includes a flexible element having a curved portion.

37. The system of claim 35, wherein when the pulmonary anchor balloon is distally disposed inside the pulmonary vein, the tissue ablation device is adjustable relative to the position of the pulmonary anchor balloon so as to form an annular area of ablated tissue along an antrum.

38. The system of claim 37, further comprising an elongate anchor catheter that is coupled to the pulmonary anchor balloon, the elongate anchor catheter and the pulmonary anchor balloon being deliverable through a guide lumen that extends through the elongate body and the distal end of the tissue ablation device.

39. The system of claim 38, wherein the pulmonary anchor balloon extends distally from the distal end of the tissue ablation device when the elongate anchor catheter is delivered through the guide lumen and out of an opening at the distal end of the tissue ablation device.

40. The system of claim 35, wherein the tissue ablation device comprises a first expandable balloon.

41. The system of claim 40, wherein the first expandable balloon defines a coolant chamber in which a cryo coolant is cycled, the coolant chamber being in fluid communication with at least one coolant lumen that extends through the elongate body.

42. The system of claim 41, wherein the tissue ablation device comprises a second expandable balloon that substantially surrounds the first expandable balloon to define a safety chamber in fluid communication with a vacuum lumen extending through the elongate body.

43. The system of claim 40, wherein the first expandable balloon defines an inflation chamber to receive a chemical solution, further comprising electrodes arranged along the inflation chamber to heat the chemical solution using RF energy.

44. The system of claim 35, wherein the elongate body comprises a first lumen in fluid communication with the tissue ablation device and a guide lumen extending centrally through the tissue ablation device to a distal opening at the distal end of the tissue ablation device, and wherein an elongate anchor member coupled to the pulmonary anchor balloon is slidably movable within the guide lumen so that elongate anchor member extends from the distal opening at the distal end of the tissue ablation device.

45. A system to treat tissue internal to a body, comprising:
an elongate body having at least one lumen extending between a proximal portion and a distal portion;
a tissue ablation device arranged at the distal portion of the elongate body, the tissue ablation device outputting ablation energy when activated by a user-controlled instrument coupled to the proximal portion of the elongate body; and
a pulmonary anchor balloon to be received inside a pulmonary vein and extend distally from a distal end of the tissue ablation device,
wherein when the pulmonary anchor balloon is received in the pulmonary vein, the tissue ablation device is biased away from axial alignment with pulmonary anchor balloon and is annularly adjustable relative to the position of the pulmonary anchor balloon from a first position in contact with a first ostial area to a second position in contact with a second ostial area, and
wherein when the pulmonary anchor balloon is distally disposed inside the pulmonary vein, the tissue ablation device is adjustable relative to the position of the pulmonary anchor balloon so as to form an annular area of ablated tissue along an antrum.

46. The system of claim 45, wherein the tissue ablation device comprises a first expandable balloon.

47. The system of claim 46, wherein the first expandable balloon defines a coolant chamber in which a cryo coolant is cycled, the coolant chamber being in fluid communication with at least one coolant lumen that extends through the elongate body.

48. The system of claim 47, wherein the tissue ablation device comprises a second expandable balloon that substantially surrounds the first expandable balloon to define a safety chamber in fluid communication with a vacuum lumen extending through the elongate body.

49. The system of claim 46, wherein the first expandable balloon defines an inflation chamber to receive a chemical solution, further comprising electrodes arranged along the inflation chamber to heat the chemical solution using RF energy.

50. The system of claim 45, wherein the elongate body has multiple lumens extending between the proximal portion and the distal portion.

51. The system of claim 50, further comprising an elongate anchor catheter that is coupled to the pulmonary anchor balloon, the elongate anchor catheter and the pulmonary anchor balloon being deliverable through a guide lumen that extends through the elongate body and the distal end of the tissue ablation device.

52. The system of claim 51, wherein the pulmonary anchor balloon extends distally from the distal end of the tissue ablation device when the elongate anchor catheter is delivered through the guide lumen and out of an opening at the distal end of the tissue ablation device.

53. The system of claim 50, further comprising a biasing portion disposed between the tissue ablation device and the pulmonary anchor balloon when the pulmonary anchor balloon is positioned distally of the tissue ablation device, the biasing portion being configured to bias the tissue ablation device away from axial alignment with pulmonary anchor balloon.

54. The system of claim 53, wherein the biasing portion includes a flexible element having a curved portion.

55. The system of claim 50, wherein the multiple lumens of the elongate body comprise a first lumen in fluid communication with the tissue ablation device and a guide lumen extending centrally through the tissue ablation device to a distal opening at the distal end of the tissue ablation device, and wherein an elongate anchor member coupled to the pulmonary anchor balloon is slidably movable within the guide lumen so that elongate anchor member extends from the distal opening at the distal end of the tissue ablation device.

56. A system to treat tissue internal to a body, comprising:
an elongate body having at least one lumen extending between a proximal portion and a distal portion;
a tissue ablation device arranged at the distal portion of the elongate body, the tissue ablation device outputting ablation energy when activated by a user-controlled instrument coupled to the proximal portion of the elongate body; and
a pulmonary anchor balloon to be received inside a pulmonary vein and extend distally from a distal end of the tissue ablation device, wherein the elongate body comprises a first lumen in fluid communication with the tissue ablation device and a guide lumen extending centrally through the tissue ablation device to a distal opening at the distal end of the tissue ablation device, and wherein an elongate anchor member coupled to the pulmonary anchor balloon is slidably movable within the guide lumen so that elongate anchor member extends from the distal opening at the distal end of the tissue ablation device, and
wherein when the pulmonary anchor balloon is received in the pulmonary vein, the tissue ablation device is biased away from axial alignment with pulmonary anchor balloon and is annularly adjustable relative to the position of the pulmonary anchor balloon from a first position in contact with a first ostial area to a second position in contact with a second ostial area.

57. The system of claim 56, wherein the tissue ablation device comprises an expandable member.

58. The system of claim 57, further comprising an elongate anchor catheter that is coupled to the pulmonary anchor balloon, the elongate anchor catheter and the pulmonary anchor balloon being deliverable through a guide lumen that extends through the elongate body and the distal end of the tissue ablation device.

59. The system of claim 58, wherein the pulmonary anchor balloon extends distally from the distal end of the tissue ablation device when the elongate anchor catheter is delivered through the guide lumen and out of an opening at the distal end of the tissue ablation device.

60. The system of claim 57, further comprising a biasing portion disposed between the tissue ablation device and the pulmonary anchor balloon when the pulmonary anchor balloon is positioned distally of the tissue ablation device, the biasing portion being configured to bias the tissue ablation device away from axial alignment with pulmonary anchor balloon.

61. The system of claim 60, wherein the biasing portion includes a flexible element having a curved portion.

62. The system of claim 57, wherein when the pulmonary anchor balloon is distally disposed inside the pulmonary vein, the tissue ablation device is adjustable relative to the position of the pulmonary anchor balloon so as to form an annular area of ablated tissue along an antrum.

63. The system of claim 62, wherein the expandable member of the tissue ablation device comprises a first expandable balloon.

64. The system of claim 63, wherein the first expandable balloon defines a coolant chamber in which a cryo coolant is cycled, the coolant chamber being in fluid communication with at least one coolant lumen that extends through the elongate body.

65. The system of claim 64, wherein the tissue ablation device comprises a second expandable balloon that substantially surrounds the first expandable balloon to define a safety chamber in fluid communication with a vacuum lumen extending through the elongate body.

66. The system of claim 63, wherein the first expandable balloon defines an inflation chamber to receive a chemical solution, further comprising electrodes arranged along the inflation chamber to heat the chemical solution using RF energy.

67. A system to treat tissue internal to a body, comprising:
an elongate member having a proximal portion and a distal portion, the elongate member including at least one lumen extending therethrough;
a tissue treatment member disposed at the distal portion of the elongate member, the tissue treatment member being in fluid communication with the lumen; and
an anchor member adjustably engaged with the tissue treatment member such that, when the anchor member extends from an opening in a distal end of the tissue treatment member and is disposed in a position at least partially in a pulmonary vein, the tissue treatment member is nonaligned with the anchor member and is annularly adjustable relative to the position of the anchor member from a first annular position in contact with a first ostial area to a second annular position in contact with a second ostial area,
wherein the elongate member includes at least first and second lumens extending therethrough, and wherein the tissue treatment member disposed at the distal portion of the elongate member so that the tissue treatment member is in fluid communication with both the first and second lumens.

68. The system of claim 67, wherein the tissue treatment member is operable to ablate tissue that contacts an outer surface of the tissue treatment member.

69. The system of claim 68, wherein when the anchor member is distally disposed in the position at least partially in the pulmonary vein, the tissue treatment member is adjustable relative to the position of the anchor member so as to form an annular area of ablated tissue along an antrum.

70. The system of claim 67, further comprising a second elongate member that is coupled to the anchor member, the second elongate member and the anchor member being passable through a guide lumen that extends through the first elongate member and the tissue treatment member so that the anchor member extends from the opening in the distal end of the tissue treatment member.

71. The system of claim 67, wherein the anchor member comprises an expandable anchor balloon having an outer surface to press against a vein wall.

72. The system of claim 67, wherein the tissue treatment member comprises an expandable ablation balloon that is nonelastically inflatable to a fixed size and is substantially nondeformable beyond the fixed size.

73. The system of claim 72, wherein the expandable ablation balloon defines a coolant chamber in which a cryo coolant is cycled, the coolant chamber being in fluid communication with the first and second lumens that extends through the first elongate member.

74. The system of claim 67, wherein the elongate body includes a plurality of lumens extending between the proximal portion and the distal portion.

* * * * *